(12) United States Patent
Jensen et al.

(10) Patent No.: US 8,036,912 B2
(45) Date of Patent: Oct. 11, 2011

(54) INTERACTIVE WEB BASED SYSTEM IN SUPPORT OF BARIATRIC PROCEDURES

(75) Inventors: Dustin R. Jensen, Loveland, OH (US); Kristin L. Jambor, Cincinnati, OH (US); Nitin K. Jain, Cincinnati, OH (US); Richard I. Lauf, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 253 days.

(21) Appl. No.: 12/112,312

(22) Filed: Apr. 30, 2008

(65) Prior Publication Data

US 2009/0276487 A1    Nov. 5, 2009

(51) Int. Cl.
*G06Q 50/00* (2006.01)
(52) U.S. Cl. .................................. 705/2; 705/3
(58) Field of Classification Search ............... 705/2, 3; 707/104.1; 348/207.11; 709/203
See application file for complete search history.

(56) References Cited

U.S. PATENT DOCUMENTS

| | | | |
|---|---|---|---|
| 4,602,280 A | 7/1986 | Maloomian |
| 4,951,197 A | 8/1990 | Mellinger |
| 4,954,954 A | 9/1990 | Madsen et al. |
| 5,412,560 A | 5/1995 | Dennison |
| 5,412,564 A | 5/1995 | Ecer |
| 5,673,691 A | 10/1997 | Abrams et al. |
| 5,836,312 A | 11/1998 | Moore |
| 5,839,901 A | 11/1998 | Karkanen |
| 5,908,301 A | 6/1999 | Lutz |
| 5,937,387 A | 8/1999 | Summerell et al. |
| 5,954,640 A | 9/1999 | Szabo |
| 6,024,699 A | 2/2000 | Surwit et al. |
| 6,032,676 A | 3/2000 | Moore |
| 6,039,688 A | 3/2000 | Douglas et al. |
| 6,083,006 A | 7/2000 | Coffman |
| 6,168,563 B1 | 1/2001 | Brown |
| 6,190,313 B1 | 2/2001 | Hinkle |
| 6,240,393 B1 | 5/2001 | Brown |
| 6,290,646 B1 | 9/2001 | Cosentino et al. |
| 6,336,136 B1 | 1/2002 | Harris |
| 6,508,762 B2 | 1/2003 | Karnieli |
| 6,510,430 B1 | 1/2003 | Oberwager et al. |
| 6,585,516 B1 | 7/2003 | Alabaster |
| 6,589,169 B1 | 7/2003 | Surwit et al. |
| 6,602,469 B1 | 8/2003 | Maus et al. |
| 6,609,068 B2 | 8/2003 | Cranley et al. |
| 6,643,385 B1 | 11/2003 | Bravomalo |
| 6,735,479 B2 | 5/2004 | Fabian et al. |
| 6,755,783 B2 | 6/2004 | Cosentino et al. |
| 6,811,516 B1 | 11/2004 | Dugan |
| 6,817,863 B2 | 11/2004 | Bisogno |
| 6,856,938 B2 | 2/2005 | Kurtz |

(Continued)

*Primary Examiner* — Le Luu
(74) *Attorney, Agent, or Firm* — Welsh Flaxman & Gitler LLC

(57) ABSTRACT

The present invention is directed to a computer-based weight loss system for supporting bariatric treatment of obesity that is accessible to both the patient and the medical practitioner. The system has a central server maintaining a library of information related to the treatment of obesity and a patient interface and a medical practitioner interface linked to the central server for uploading and downloading of information. The patient interface also provides access to information selected from the group consisting of bariatric care pathway, behavioral modification planning, fitness, preoperative diet, postoperative diet, monitoring of a gastric band, monitoring of a patient's weight, monitoring caloric intake and nutritional information. The uploaded information is processed by the central server and then made available to the medical practitioner and the patient.

18 Claims, 47 Drawing Sheets

U.S. PATENT DOCUMENTS

| | | |
|---|---|---|
| 6,872,077 B2 | 3/2005 | Yeager |
| 6,953,342 B2 | 10/2005 | Bisogno |
| 6,968,375 B1 | 11/2005 | Brown |
| 6,974,075 B1 | 12/2005 | Duke |
| 6,980,999 B1 | 12/2005 | Grana |
| 7,063,665 B2 | 6/2006 | Hasegawa et al. |
| 7,090,638 B2 | 8/2006 | Vidgen |
| 7,177,699 B2 | 2/2007 | Fabian et al. |
| 7,189,191 B2 | 3/2007 | Dugan |
| 2003/0211007 A1 | 11/2003 | Maus et al. |
| 2004/0007240 A1 | 1/2004 | Peplinski et al. |
| 2004/0037738 A1 | 2/2004 | Maus et al. |
| 2004/0038389 A1 | 2/2004 | Maus et al. |
| 2004/0044560 A1 | 3/2004 | Giglio et al. |
| 2004/0049355 A1 | 3/2004 | Maus et al. |
| 2004/0131227 A1 | 7/2004 | Bravomalo et al. |
| 2004/0176666 A1 | 9/2004 | Chait |
| 2004/0225533 A1 | 11/2004 | Cosentino et al. |
| 2005/0004436 A1 | 1/2005 | Nissila et al. |
| 2005/0113649 A1 | 5/2005 | Bergantino |
| 2005/0113650 A1 | 5/2005 | Pacione et al. |
| 2005/0240444 A1 | 10/2005 | Wooten et al. |
| 2005/0266385 A1 | 12/2005 | Bisogno |
| 2006/0015016 A1 | 1/2006 | Thornton |
| 2006/0116558 A1 | 6/2006 | Jang et al. |
| 2006/0161458 A1 | 7/2006 | Lauzon |
| 2006/0178912 A1 | 8/2006 | Ferraro et al. |
| 2006/0189853 A1 | 8/2006 | Brown |
| 2006/0199997 A1 | 9/2006 | Hassler, Jr. et al. |
| 2006/0229504 A1 | 10/2006 | Johnson, Jr. |
| 2006/0235280 A1 | 10/2006 | Vonk et al. |
| 2007/0027366 A1 | 2/2007 | Osburn |
| 2007/0136093 A1 | 6/2007 | Rankin et al. |
| 2009/0089088 A1* | 4/2009 | Schoenberg ............... 705/2 |
| 2009/0150439 A1* | 6/2009 | Gejdos et al. ............. 707/104.1 |
| 2009/0157426 A1* | 6/2009 | Malec et al. ............... 705/3 |
| 2009/0171696 A1* | 7/2009 | Allard et al. .............. 705/3 |
| 2009/0254361 A1* | 10/2009 | Schoenberg ............... 705/2 |
| 2010/0026817 A1* | 2/2010 | Ryan et al. ............... 348/207.11 |

* cited by examiner

Realize mySuccess

Login

*Required

New to REALIZE mySUCCESS?

Congratulations on your decision. You now have access to your own personal support system - REALIZE mySUCCESS - as you prepare for surgery and as you progress after Realize™ Band surgery Register Now

Already Registered?

* Username (email):
patient@realizeband.com

* Password:
******

☑ Remember my username

Login

Forgot password?

Terms of Use | Privacy Policy | Contact Us

Ethicon Endo-Surgery, Inc. 2007. All rights reserved. DSL#07-1858. REALIZE™ and REALIZE mySUCCESS™ are trademarks of Ethicon Endo-Surgery, Inc. This site is published by Ethicon Endo-Surgery, Inc. which is solely responsible for its contents; it is intended for US residents only. This site is not intended as a substitute for professional medical care. Only your physician can diagnose and appropriately treat your symptoms.

Realize | mySuccess™

Welcome, Margaret
Log Out | My Profile
Cincinnati Bariatric Center (513) 555-1234 myGoals

Goals Achieved

| Achieved | Goal/Description |
|---|---|
| Aug 18, 2007 | Educate my family on weight loss surgery be... Talk to each family nmber about my d... |
| May 29, 2007 | REALIZE Band surgery on May 29 Begin my journey to a healthier me! |

Goals in Progress — 52 — ⊕ Add

| Date | Goal/Description |
|---|---|
| Nov 26, 2007 | Avoid unplanned holiday snacks I can say "no" to junk food and unplan.... |
| Nov 24, 2007 | I don't want to hurt every morning Less weight means less stress on my jo.... |
| Nov 12, 2007 | Walk in the 2008 Race for the Cure Increase my stamina and improve my fil... |

Setting Goals

Your weight loss is a means to a healthier, more active, more confident you. Setting and achieving goals is a critical part of your success. Use this service to track your progress with personal objectives that really matter to you: being able to get down on the floor and play with your kids, lowering your high blood pressure, wearing more fashionable clothing, fitting into stadium and theater seats, or feeling more confident around others.

View All Articles

Ethicon Endo-Surgery, Inc. 2007. All rights reserved. DSU#07-1858, REALIZE™ and REALIZE mySUCCESS™ are trademarks of Ethicon Endo-Surgery, Inc. This site is published by Ethicon Endo-Surgery, Inc. which is solely responsible for its contents. It is intended for US residents only. This site is not intended as a substitute for professional medical care. Only your physician can diagnose and appropriately treat your symptoms.

Terms of Use | Privacy Policy | Contact Us

Realize | mySuccess™ myNutritionPlan

Welcome, Margaret
Log Out | My Profile
Cincinnati Bariatric Center (513) 555-1234

Your Personal Nutrition Plan

You are embarking on a journey to make permanent diet and lifestyle changes. Your eating plan after surgery is the way medical and health experts say we should all be eating. This is not another "diet"; it is a healthy eating plan. In the myNutritionPlan section of myPersonalPlan, you can proactively determine how to best give your body the nutrition it needs, not only during your weight loss but as you enjoy your healthy lifestyle in the years to come.

Recovery Eating Plan

Recovery may last six to eight weeks. During this time, you will gradually progress from clear liquids to solid foods along a plan your healthcare team recommends. The eating plan presented here is general and may be different from the one your healthcare team recommends. There may also be differences based on health restrictions, e.g., if you are diabetic or have a heart condition. As always, follow your healthcare team's directions.

Clear liquids: Clear liquids consist of foods and beverages that you can see through at room temperature. They contain minimal residue and promote the digestive progress. Choose clear liquids that are sugar-free and non-carbonated. The clear liquids phase generally includes foods like clear broth, sugar-free gelatin, sugar-free ice pops, sugar-free flavored drinks, coffee and tea.

myNutritionPlan Goals ⊕Add

<u>Drink enough fluids</u>
1. Half of fluids should come from water.
2. Sip 64 oz. slowly during the day.
3. Stick with a low-calorie, non-carbonated beverages.

<u>Eliminate grazing</u>
1. Avoid the office candy dish.
2. Don't eat off Katie's plate.
3. Avoid taste testing while cooking.

<u>Good Portion Control</u>
1. Measure food.
2. Use a small plate.
3. Eat about 1/2 cup per meal.

Ethicon Endo-Surgery, Inc. 2007. All rights reserved. DSU#07-1853, REALIZE™ and REALIZE mySUCCESS™ are trademarks of Ethicon Endo-Surgery, Inc. This site is published by Ethicon Endo-Surgery, Inc. which is solely responsible for its contents. It is intended for US residents only. This site is not intended as a substitute for professional medical care. Only your physician can diagnose and appropriately treat your symptoms.

Terms of Use | Privacy Policy | Contact Us

FIG. 25

Realize | mySuccess™

Welcome, Margaret
Log Out | My Profile
Cincinnati Bariatric Center (513) 555-1234 myTemptations

Your Personal Temptations

Identifying, preventing and managing your emotional eating triggers and temptations are very important for long-term success. Emotional eating, sometimes known as "comfort eating," "head hunger," or "mouth hunger," can generally be defined as eating for any reason other than true physical hunger. Triggers can come in the form of experiences both internal (thoughts and feelings) and external (sights, sounds, and smells of food) that cause you to be tempted to eat, even when you are not physically hungry.

"Head Hunger"

Internal triggers are common feelings and thoughts that may cause an impulse to eat for reasons other than hunger. It is absolutely critical that you learn to identify whether or not you are truly hungry, or if you are just experiencing "head hunger" or "mouth hunger." Unless you are truly physically hungry, the urge will pass if you can redirect your attention for 10 or 15 minutes.

Many people instinctively recognize their eating triggers and temptations. Common internal triggers are negative feelings such as anger, sadness, frustration and loneliness. People are also triggered by positive emotions such as happiness or a celebration. Even neutral feelings such as boredom or being tired can be eating triggers. If you are uncertain about your triggers or if you have a problem with emotional eating, keeping a food/feeling journal can be a good way to identify these issues. If you continue to be unsuccessful in managing your pattern on eating for emotional reasons, consider getting some professional help from a therapist or counselor.

myTemptations  ⊕ Add

Don't eat when anxious -- exercise!
1. Breathe!
2. Practice my stretching exercises.
3. Take a walk with my favorite music.

Celebrate happiness without food
1. Share my happiness with friends.
2. Embrace the feeling!
3. Celebrate with non-food rewards.

Relieve stress without eating
1. Make time to enjoy a hot bath.
2. Practice my meditation exercises.
3. Plan a night out with Jim - no kids.

Ethicon Endo-Surgery, Inc. 2007. All rights reserved. DSU#07-1858, REALIZE™ and REALIZE mySUCCESS™ are trademarks of Ethicon Endo-Surgery, Inc. This site is published by Ethicon Endo-Surgery, Inc. which is solely responsible for its contents. It is intended for US residents only. This site is not intended as a substitute for professional medical care. Only your physician can diagnose and appropriately treat your symptoms.

Terms of Use | Privacy Policy | Contact Us

FIG. 27

Realize | mySuccess™ mySuccessStrategies

Welcome, Margaret
Log Out | My Profile
Cincinnati Bariatric Center (513) 555-1234

Strategies for Facing Challenges

As you become comfortable with your new way of eating, life will throw you a curve ball. You may encounter people or situations that may not support your new healthy eating practices.

Eating out, eating with other people, celebrations, vacation all can pose challenges to your new lifestyle. At times, you may feel that you are not well supported by friends and family. Your best line of defense is pre-planning. Planning ahead is critical because it allows you to anticipate difficulties and strategize effective ways to cope with them.

In this part of myPersonalPlan, you can anticipate the challenges you are most likely to face and plan ways to effectively meet those challenges. Choose three or four areas from the drop-down menu that are particularly difficult for you, or add your own. Read the suggestions for coping with these situations, and develop plans that will work for you. Facing challenges beforehand prepares you for success.

Social Events And Special Occasions

Social events often seem to revolve around food. Celebrations, times of sadness, holidays, family gatherings all can be times where food holds a central place. You may feel that social engagements are less enjoyable because many of the the high-calorie foods and beverages served are not part of your healthy eating plan.

You may feel pressure to eat when you are not hungry. Are you concerned that it will draw attention if you makes you feel this way. Ask yourself what mySuccessStrategies                         ⊕ Add

Involving Your Kids
1. Let Katie and Matt help plan, shop and cook.
2. Remember -- I am a role model for my children.

Dealing with Saboteurs
1. Explain the health benefits you are experiencing.
2. Be honest and ask for support.
3. Find supportive friends and family.

Eating in Restaurants
1. Ask for dressing and sauces on the side.
2. Request a doggie bag before my food is served.
3. Substitute healthier options, like veggies for fries.

Ethicon Endo-Surgery, Inc. 2007. All rights reserved. DSU#07-1858, REALIZE™ and REALIZE mySUCCESS™ are trademarks of Ethicon Endo-Surgery, Inc. This site is published by Ethicon Endo-Surgery, Inc. which is solely responsible for its contents. It is intended for US residents only. This site is not intended as a substitute for professional medical care. Only your physician can diagnose and appropriately treat your symptoms.

Terms of Use | Privacy Policy | Contact Us

FIG. 28

Realize | mySuccess ™

Welcome, Margaret
Log Out | My Profile
Cincinnati Bariatric Center (513) 555-1234 mySupportTeam

Your Support Team

Your support network is your very own personal cheering section-family members, friends, website communities/online buddies, practice staff, support groups, and healthcare professionals. Your support network can include anyone with whom you can honestly share your thoughts and feelings during and beyond your Realize™ Surgery journey.

Among the people in your support network, see if there is at least one person that you can count on almost 24/7 to be there for you in times of need and times of celebration! There will be moments when you could use a pep talk, advice, information, and ideas for coping with challenges; there will be other moments when you could use just plain TLC. Some lucky people have a devoted spouse, partner or other loved ones right in their home. Others have a good friend or support person just a phone call or mouse click away. Your practice's post-op support group may be able to provide the kind of help that can only come from those who have experienced weight loss surgery success themselves.

Here are some suggestions to help you build your own support network. Your list doesn't need to be long - just get started. If you need some help deciding whom to include, talk to one of the professionals at your surgeon's practice or your support group.

Support from Family and Friends
Who: Your Spouse/Partner/Significant Other
How he/she can help: A supportive relationship can make all the difference in your day-to-day weight loss journey. A general source of mySupportTeam Resources       ⊕ Add

Spouse/partner/significant other
1. Take a walk every evening.
2. Prepare meals together.

Extended Family
1. Exercise together.
2. Share recipes.
3. Make family gatherings less food-oriented.

Friends
1. Enlist friends to support my healthy lifestyle.
2. Let my friends know how much I appreciate their help.
3. Call Jane when I need extra help resisting food.

Ethicon Endo-Surgery, Inc. 2007. All rights reserved. DSU#07-1858. REALIZE™ and REALIZE mySUCCESS™ are trademarks of Ethicon Endo-Surgery, Inc. This site is published by Ethicon Endo-Surgery, Inc. which is solely responsible for its contents. It is intended for US residents only. This site is not intended as a substitute for professional medical care. Only your physician can diagnose and appropriately treat your symptoms.

Terms of Use | Privacy Policy | Contact Us

Realize mySuccess™

- Home
- onTrack Alerts
- New Patient Codes
- myPatients
- Patient Content
- Using Realize mySuccess™
- myAccount
- User Administration
- ■ Help
- Logout

Help

Frequently Asked Questions

Why don't all the links work for me?
How do I view/manage onTrack alerts?
How do I issue Surgeon's Practice ID codes?
How do I view a list of all our patients?
How do I view Realize mySuccess™ information for a particular patient?
What is a User Administrator?
How does a User Administrator set up new users or modify user profiles?
How do patients register for REALIZE mySUCCESS?
How can I print what I see on the screen?
Is REALIZE mySUCCESS training available?
Who can I contact for customer support?
Can I see what patients see on REALIZE mySUCCESS?
How do I register a patient for REALIZE mySUCCESS who has lost the Realize™ Medical Information Card containing his or her Patient Card ID?
Once I am set up as a user by the User Administrator, can I modify my own account?
Can I search for or sort my patients by criteria other than last name?
What are the latest updates to REALIZE mySUCCESS for Practices?
How do I enter a security question?

back to top

Why don't all the links work for me?

Not all areas of REALIZE mySUCCESS are appropriate for all users. If not all of the navigational links work for you, and you feel you need additional access, contact your office's designated User Administrator.

How do I view/manage onTrack Alerts?

All onTrack Alerts within the last seven days, regardless of surgeon, are shown by default. Results may be filtered by surgeon, alert and time period (days) by selecting from the appropriate drop-down menu and clicking the Show Results button. It is best to check these

INTERACTIVE WEB BASED SYSTEM IN SUPPORT OF BARIATRIC PROCEDURES

BACKGROUND OF THE INVENTION

1. Field of the Invention

The invention relates to a computer system providing assistance in bariatric treatment, for example, procedures aimed at treating obesity. More particularly, the invention relates to a computer system working in conjunction with gastric (or other bariatric) procedures to assist patients and medical practitioners in the treatment of obesity.

2. Description of the Related Art

Obesity has become a major problem in our society. Activities which previously required substantial manual exertion now are accomplished with minimal effort. Processed food is also more plentiful and provides people with ready access to high calorie food, and often times, facilitates over eating.

A portion of the population requires surgical intervention to address and alleviate the problems associated with their obesity. These surgical procedures may range from restriction of the stomach to a complete rearrangement of the digestive system. Each of these procedures comes with its own host of complications and advantages.

One procedure that has recently grown in popularity is adjustable gastric band application employed in reducing stomach volume and ultimately reducing food intake. Regardless of which procedure is chosen to address a person's obesity problem, these people require support both before and after the procedure. The present invention provides a system for supporting both the patient undergoing obesity related procedures and the medical practitioner assisting them in achieving their goal of losing weight and ultimately improving their quality of life.

SUMMARY OF THE INVENTION

It is, therefore, an object of the present invention to provide a computer-based weight loss system for supporting bariatric treatment of obesity that is accessible to both the patient and the medical practitioner. The system includes a central server maintaining a library of information related to the treatment of obesity. The system also includes a patient interface linked to the central server, wherein the patient interface provides for uploading and downloading of information to the central server. The uploaded information is processed by the central server and then made available to the medical practitioner and the patient. The patient interface also provides access to information selected from the group consisting of bariatric care pathway, behavioral modification planning, fitness, preoperative diet, postoperative diet, monitoring of a gastric band, monitoring of a patient's weight, monitoring caloric intake and nutritional information. It is another object of the present system to provide a system including a medical practitioner interface linked to the central server. The medical practitioner interface provides for uploading and downloading of information to the central server. The uploaded information is processed by the central server and then made available to the medical practitioner and the patient.

It is also an object of the present invention to provide a computer-based weight loss system wherein the central server integrates information from a plurality of medical practices.

It is another object of the present invention to provide a computer-based weight loss system wherein the system generates alerts to the patient and medical practitioners via the respective patient interface and the medical practitioner interface.

It is a further object of the present invention to provide a computer-based weight loss system wherein the medical practitioner interface also provides a means for the medical practitioner to retrieve, edit and control information uploaded by the patient.

It is also an object of the present invention to provide a computer-based weight loss system wherein the patient interface includes tools selected from the group consisting of tools designed to assist the patient in continuing to develop personalized eating and fitness plans, tools designed for envisioning the new person the patient will become, tools allowing access to healthy recipes, tools for setting up appointments and reminders, and tools for developing strategies for meeting personal challenges.

It is another object of the present invention to provide a computer-based weight loss system wherein the patient interface includes a homepage and the homepage provides the user with access to tools respectively grouped in a personal plan focused section, a nutrition focused section, a fitness focused section, and a progress focused section relating to a patient's weight.

It is a further object of the present invention to provide a computer-based weight loss system wherein the personal plan focused section includes a tool allowing the patient to identify and focus on the results that mean the most to him or her, a tool allowing the patient to record their weight and measurements and view a visual representation of their progress to date, a tool allowing the patient to record filling of the gastric band and participate in band adjustment surveys, a tool allowing the patient to store a plurality of photos and create a photo journal of the patient's progress as he or she loses weight, and a tool allowing the patient to create virtual images based on height, weight and body type.

It is also an object of the present invention to provide a computer-based weight loss system wherein the nutrition focused section includes a food diary tool and a recipes tool.

It is another object of the present invention to provide a computer-based weight loss system wherein the food diary tool allows patients to track what and where they eat, their mood during meals, how well the food was tolerated and if the food was planned.

It is a further object of the present invention to provide a computer-based weight loss system wherein the recipes tools includes access to gastric band-friendly recipes.

It is also an object of the present invention to provide a computer-based weight loss system wherein the fitness focused section includes a fitness planning tool and a fitness diary tool.

It is another object of the present invention to provide a computer-based weight loss system wherein the personal plan focused section includes a tool allowing patients to elect to be notified of appointments and reminded of tasks critical to success by electronic means to wired or wireless devices, such as, email, text message or at log-in, a tool encouraging patients to focus on preplanned meals, a tool allowing patients to identify times they are most apt to eat for reasons other than hunger, a tool allowing patients to develop coping strategies for potential stumbling blocks, and a tool allowing patients to identify the family, friends and healthcare providers they rely upon most.

It is a further object of the present invention to provide a computer-based weight loss system wherein the medical practitioner interface includes a medical practice homepage where the medical practitioner is provided with practice statistics and navigation tools including information on patient registration, alerts, frequency of use, and how many pounds patients have lost using the designated gastric band procedure.

It is also an object of the present invention to provide a computer-based weight loss system wherein the medical practitioner interface includes a patient's food diary tool, an alert tool, a gastric band adjustment tool and a patient activity level tools.

It is another object of the present invention to provide a computer-based weight loss system wherein the medical practitioner interface provides an alert tool.

It is a further object of the present invention to provide a computer-based weight loss system wherein the alert tool allows medical practitioners to identify issues they may want to address with their patients.

It is also an object of the present invention to provide a computer-based weight loss system wherein the alert tool include alerts relating a band adjustment survey, a predetermined increment of weight loss, a weight gain over a predetermined time period, a weight plateau for a predetermined time period, a no band adjustment for a predetermined time period after surgery, a changes practice affiliation, a no logged weight for a predetermined time period, a no logged site access for a predetermined time period.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 4-46 are various screen shots of the interfaces employed in accordance with the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

In accordance with the present invention, and with reference to FIGS. 1 to 46, a computer-based weight loss system 10 for assisting patients and medical practitioners in the treatment of obesity is provided. As used herein, the term medical practitioner is considered to include surgeons, doctors, dieticians, physiologists, nurses, etc. The present computer-based weight loss system 10 applies system intelligence to up-to-date patient-reported data, enabling medical practitioners to proactively intervene before minor setbacks in behavior modification turn into patient hopelessness, guilt, and ultimately failure. The present computer-based weight loss system 10 aids the patient and medical practitioner throughout the entire process, providing tools which assist with regard to both preoperative issues and postoperative issues.

Although the present computer-based weight loss system 10 is particularly adapted for medical practitioners focusing on the treatment of obesity through the utilization of gastric band treatment, access thereto may be provided to other medical practitioners in consideration of the fact much of the treatment for obesity overflows into other medical specialties and the information available via the present computer-based weight loss system 10 would certainly be of interest to a variety of medical practitioners not only those specializing in bariatric procedures. For example, it might be advantageous to integrate data from practice electronic record or Centers of Excellence (an ASMBS (American Society for Metabolic and Bariatric Surgery) certification) database to facilitate two-way communication potential.

Figure 1:
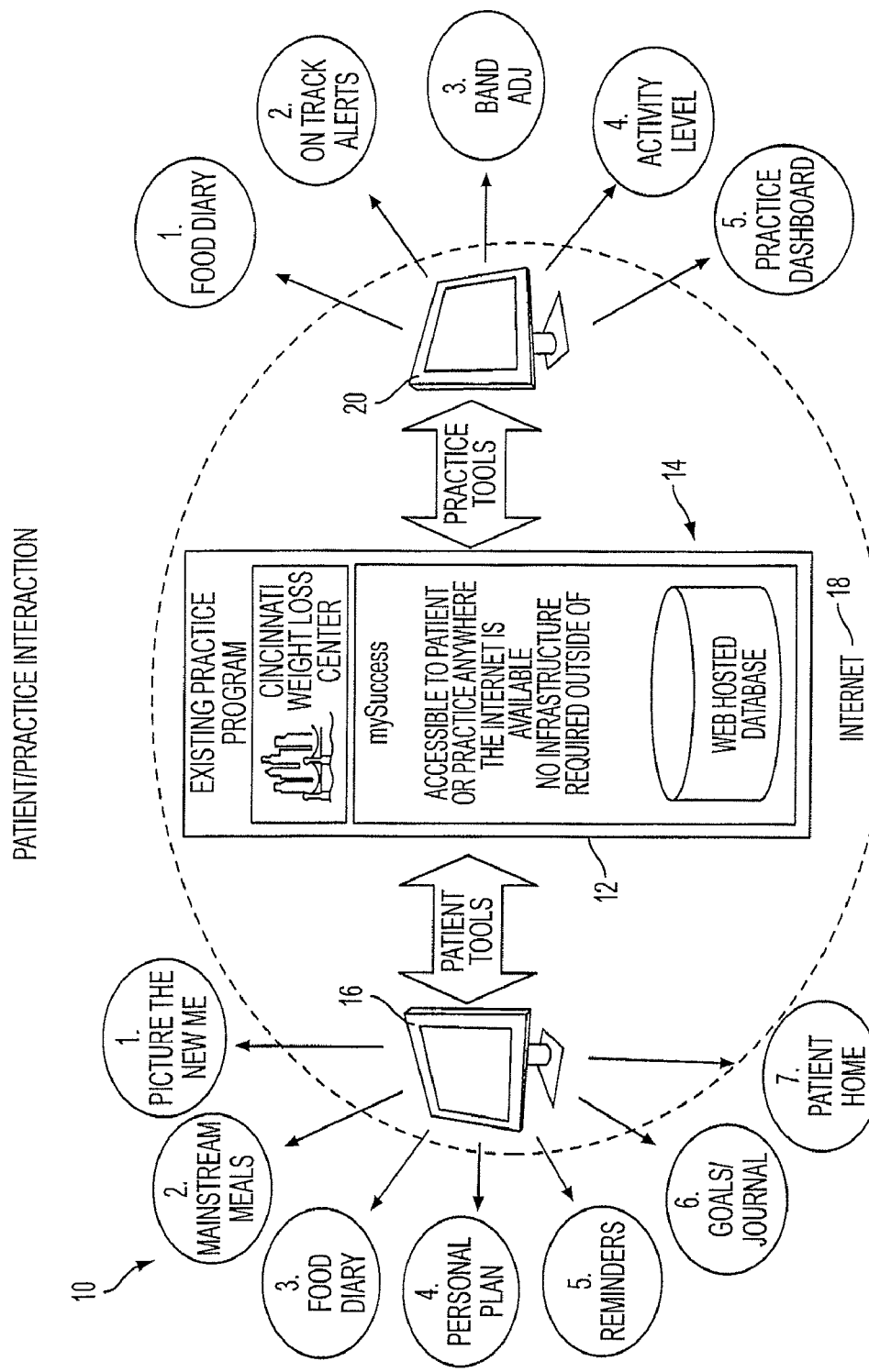
FIG. 1 is a schematic of the present computer-based weight loss system.

Referring to the network diagram shown in FIG. 1, the system 10 includes a central server 12 maintaining a library of information 14 related to the treatment of obesity. In accordance with a preferred embodiment of the present invention, the central server 12 is a computer database allowing for the input and retrieval of information in a highly efficient manner. The system 10 further includes a patient interface 16 linked to the central server 12. In accordance with a preferred embodiment of the present invention, the patient interface 16 is a graphical user interface accessed via a computer connected to a global communication network, for example, the Internet 18, for interaction with the central server 12. The patient interface 16 provides for uploading and downloading information to and from the central server 12. The uploaded information is processed by the central server 12 and then made available to the medical practitioner and the patient. The patient interface 16 also provides access to information stored within the central server 12. The information is selected from the group consisting of bariatric care pathway, behavioral modification planning, fitness, preoperative diet, postoperative diet, monitoring of a gastric band, monitoring of a patient's weight, monitoring caloric intake, nutritional information, as well as other information sources discussed throughout the present disclosure. As will be discussed below in greater detail, the present computer-based system 10 generates data that is available to medical practitioners and similarly issues relevant alerts to the patient via the patient interface 16.

The computer-based weight loss system 10 also includes a medical practitioner interface 20 linked to the central server 12. In accordance with a preferred embodiment of the present invention, the medical practitioner interface 20 is a graphical user interface accessed via a computer connected to a global communication network, for example, the Internet 18 for interaction with the central server 12. The medical practitioner interface 20 provides for uploading and downloading information to and from the central server 12. The information is processed by the central server 12 and then made available to the medical practitioner (and particularly the patient). The medical practitioner interface 20 also provides access to information selected from the group consisting of bariatric care pathway, preoperative diet, postoperative diet, monitoring of a gastric band, monitoring of a patient's weight, monitoring caloric intake, a list of appropriate foods, as well as other information sources discussed throughout the present disclosure.

The medical practitioner interface 20 also provides a mechanism for the medical practitioner to access, monitor and modify all information available throughout the present computer-based weight loss system 10; that is, the medical practitioner is provided with "back end" access via the medical practitioner interface 20 allowing for retrieval, editing and control of information input and accessed by the patient. In addition, and as will be discussed through out the present disclosure, the medical practitioner interface 20 allows the medical practitioner to access patient information for the purpose of improving successful outcomes and associated benefits, optimizing the utilization of the present computer-based weight loss system 10 in assisting the patient in his or her weight loss. As will be discussed below in greater detail, the present computer-based weight loss system 10 generates data that is made available to medical practitioners via the medical practitioner interface 20. In addition, it is contemplated medical practitioners may have the ability to contact the patient using email addresses and/or contact information stored by the central server 12.

As those skilled in the art will appreciate, the present weight loss system 10 is computer-based and relies upon the protocols of the Internet 18, or other global communication network, to allow for the transfer of information between the patient interface 16, medical practitioner interface 20 and the central server 12 to achieve the purposes and functionalities discussed below in accordance with a preferred embodiment of the present invention. While a preferred mode of implementation is discussed below, those skilled in the art will appreciate data transfer via various networks is quickly developing and it is contemplated various modes of implementation may be employed without departing from the spirit of the present invention.

Figure 2:
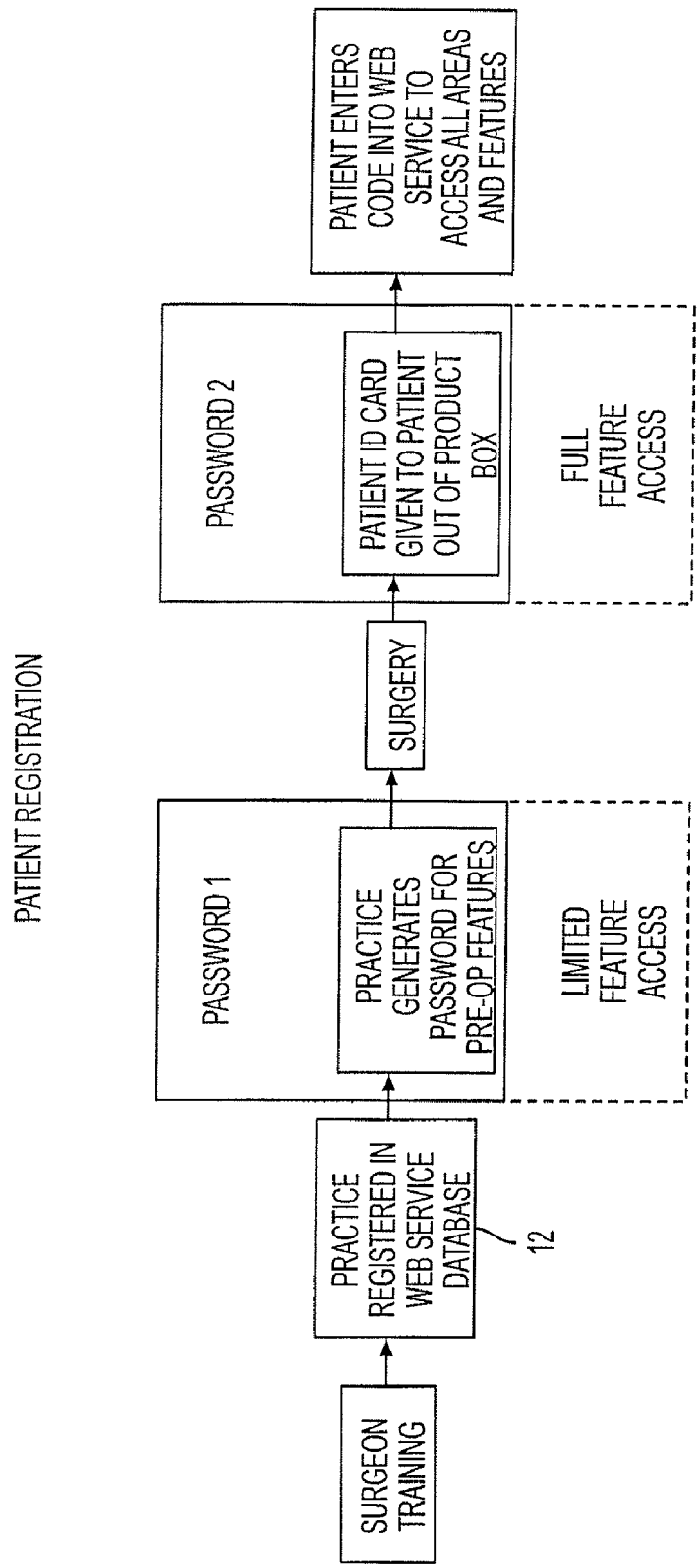
FIG. 2 is a flow chart relating to patient registration in accordance with the present invention.
Figure 3A:
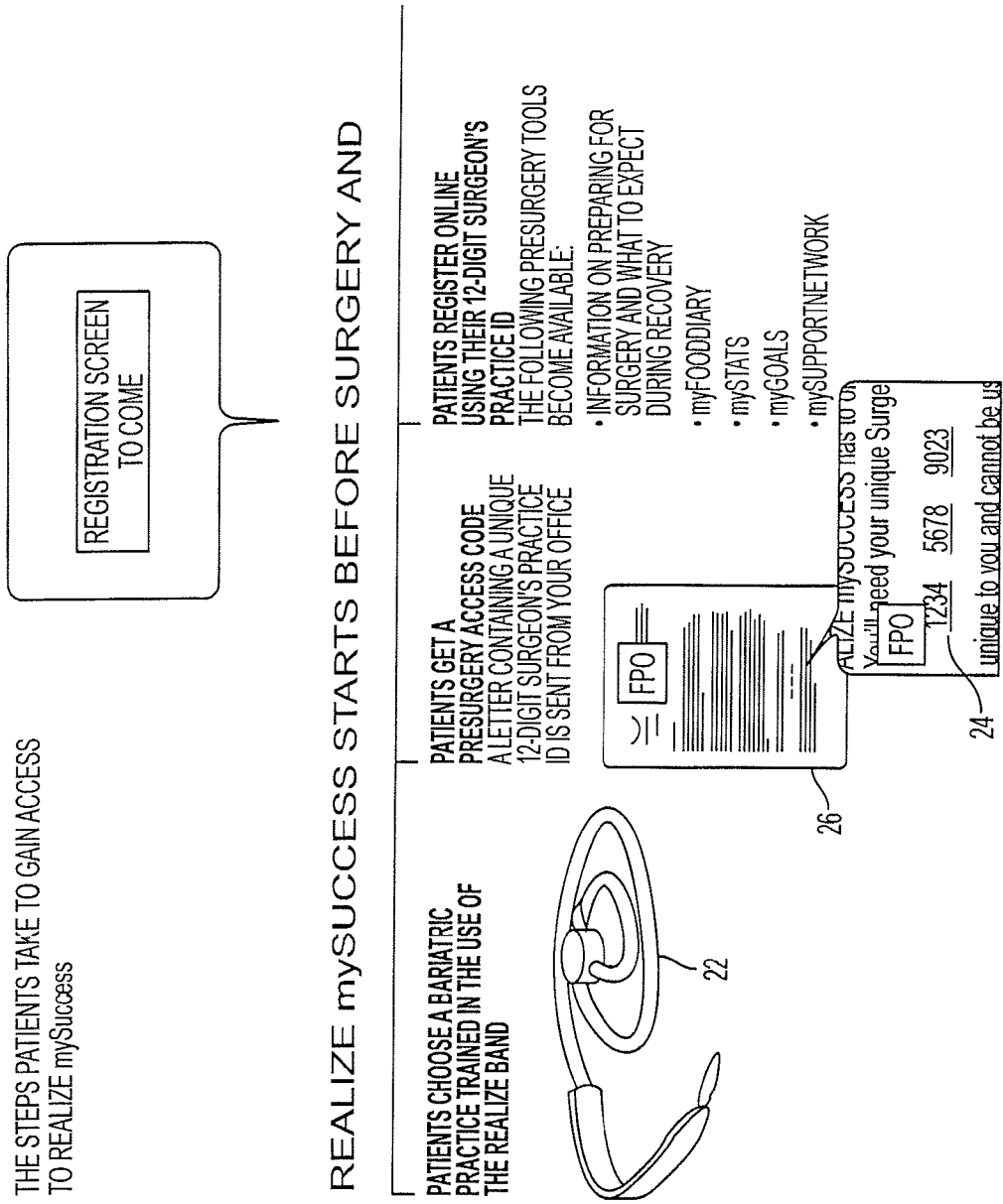
FIGS. 3A and 3B are a flow chart relating to operation of the present computer based weight loss system.
Figure 3B:
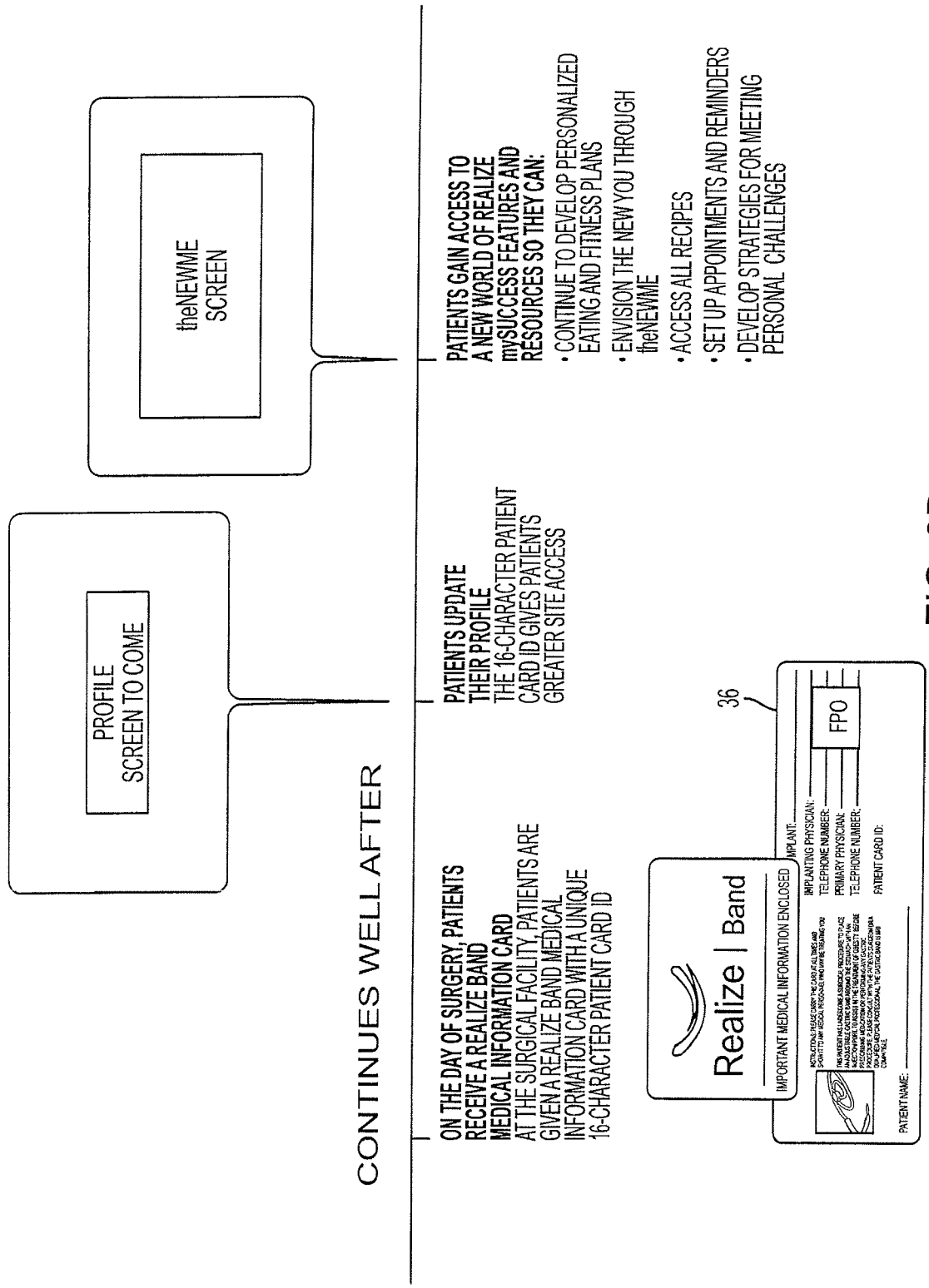
Figure 6:
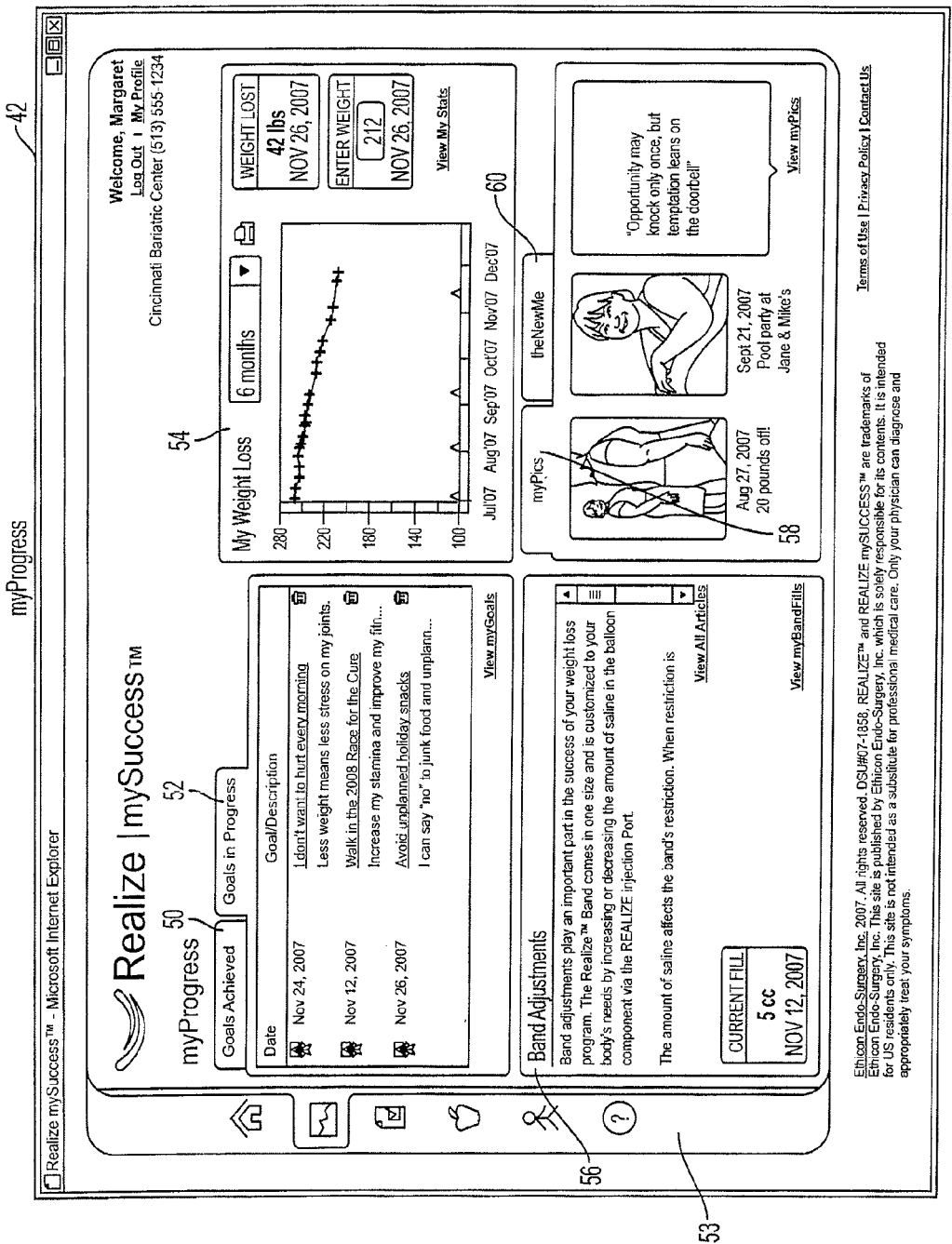
Figure 8:
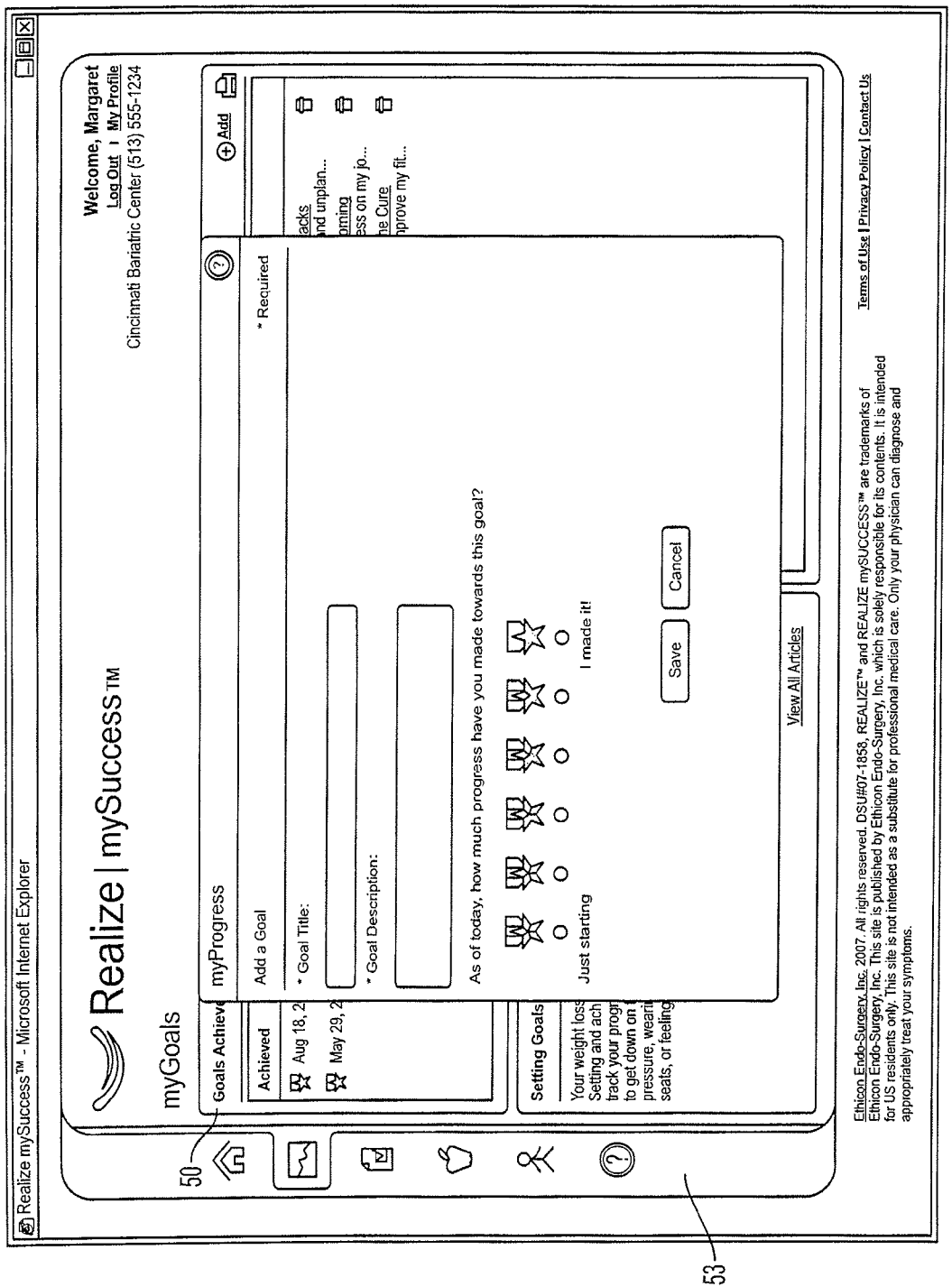
Figure 11:
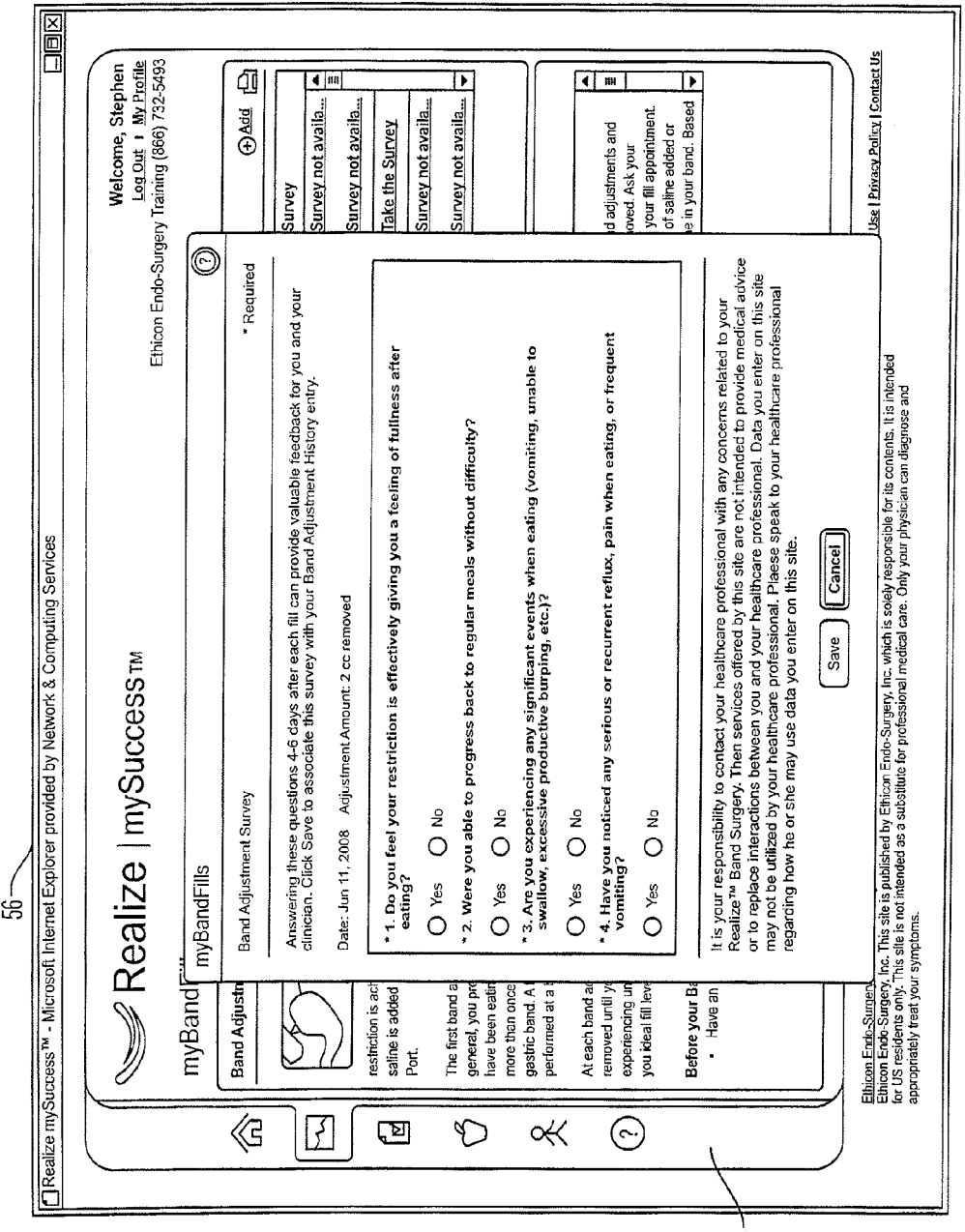
Figure 12:
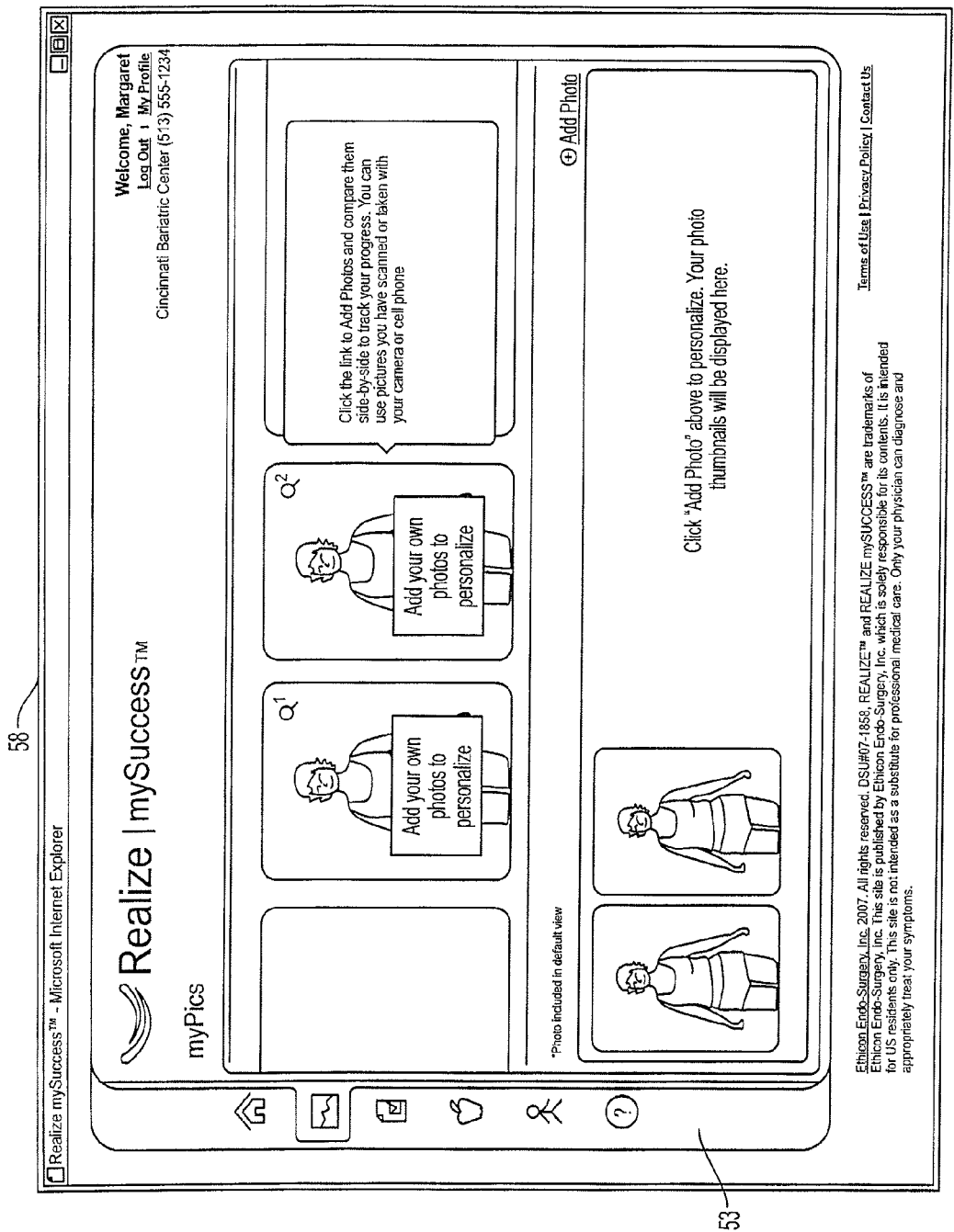
Figure 13:
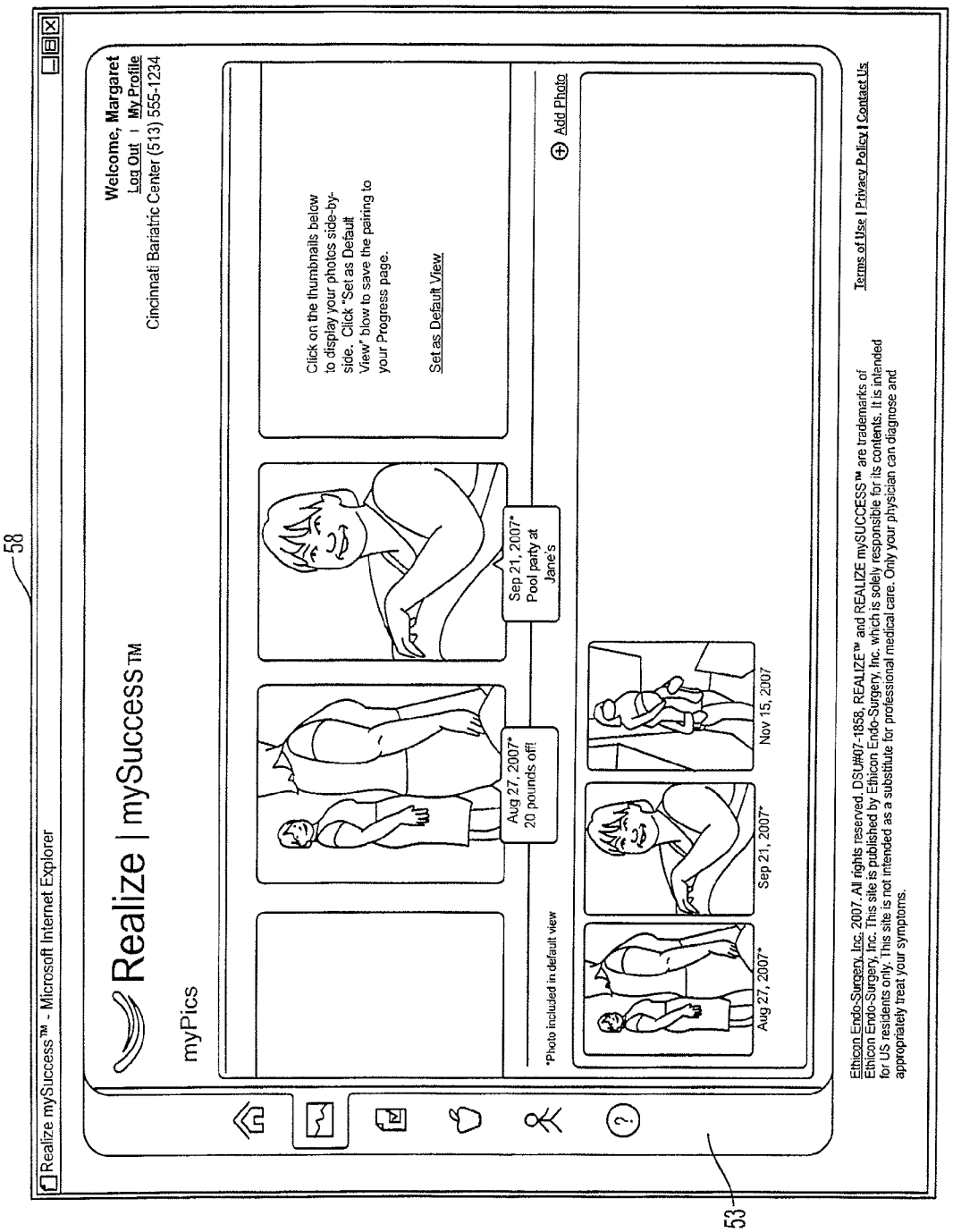
Figure 14:
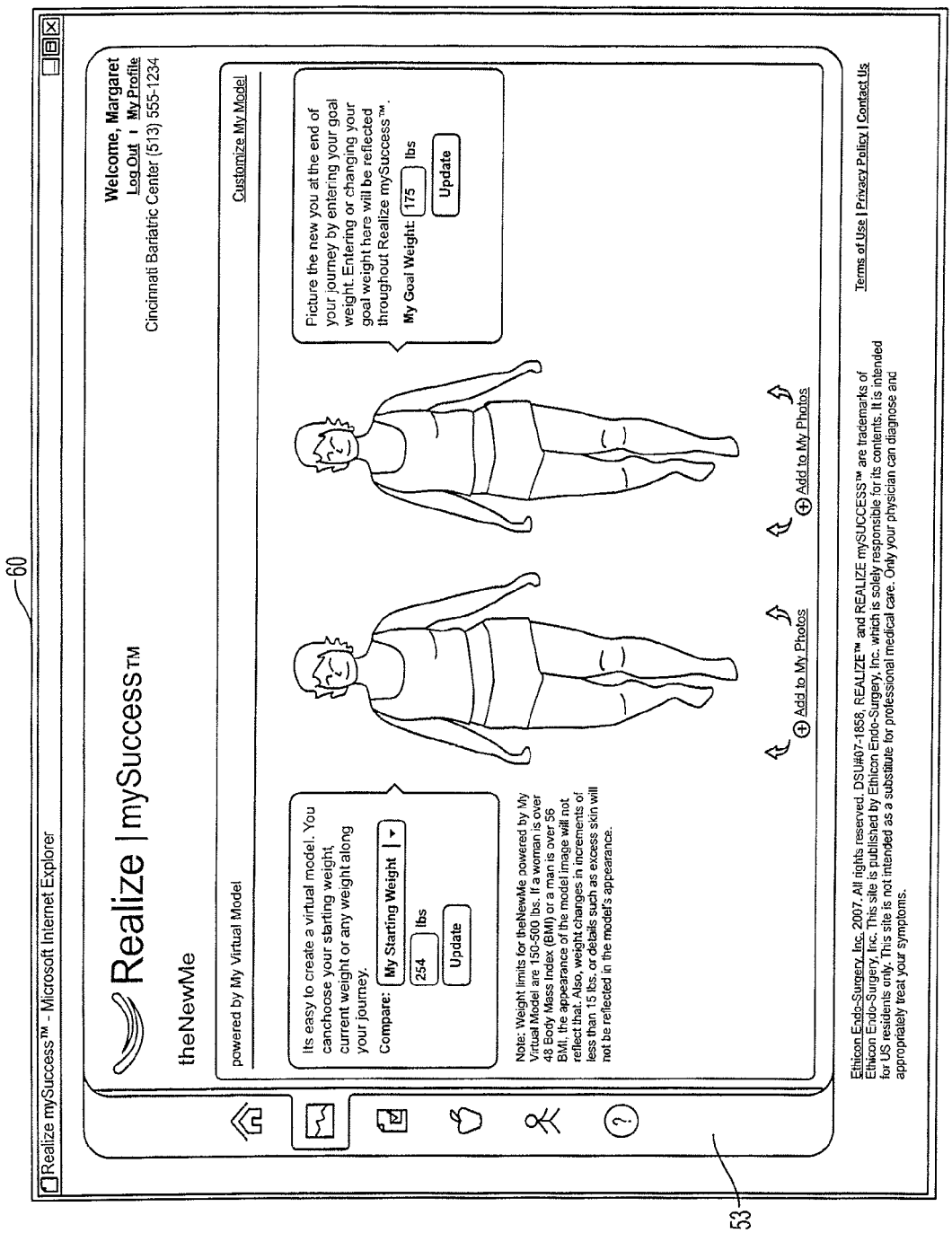
Figure 15:
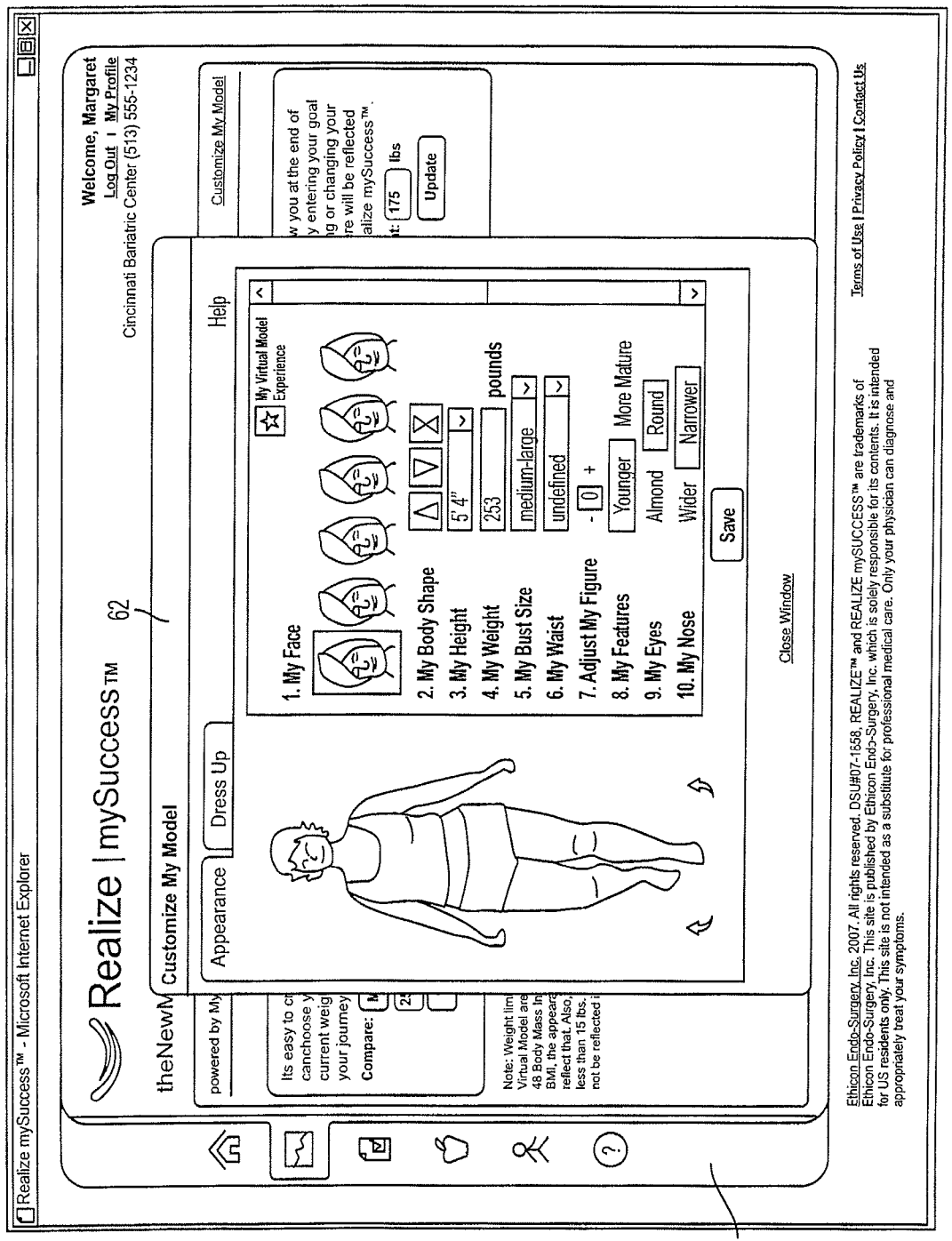

In use, and in accordance with a preferred embodiment of the present invention as disclosed with reference to FIGS. 2, 3A and 3B, a medical practice initiates use of the present computer-based weight loss system 10 by undergoing a training procedure in the use of gastric bands 22 complying with the requirements of the present computer-based weight loss system 10, as well as the use of the computer-based weight loss system 10 itself. The medical practitioner then registers with the web service database of the central server 12. Thereafter patients are provided access to the present computer-based weight loss system 10 for use in facilitating weight reduction through consultation with approved medical practices.

After meeting with a medical practitioner specializing in the field of bariatric surgery, the patient is provided with limited access to the present computer-based weight loss system 10 for accessing information regarding pre-operative information relevant to the patient's specific situation. In accordance with a preferred embodiment, the medical practitioner presents a limited access ID code 24 to the patient. The limited access ID code 24 allows the patient access to information specifically designed for that medical practitioner and useful to the patient as he or she makes treatment decisions. The ID code 24 may also allow the patient to access information developed specifically for a medical practice group. Ultimately, the operators of the computer-based weight loss system 10 and/or the medical practitioner control the amount of information to which the patient may receive access.

In accordance with a preferred embodiment, to register a new user on the present computer-based weight loss system 10, the patient will need a valid email address and a surgeon's practice ID code (that is, the limited access ID code) 24, which is supplied by the medical practitioner. Each time an ID code 24 is generated, it is printed on a letter 26 given to a patient with instructions to complete the registration process. New ID codes (and letters) may be printed for patients who have lost or forgotten their original ID code. The medical practitioner need not record a patient's ID code 24. It should be understood that these ID codes 24 are unique both for the medical practitioner and the patient. As such, each patient wishing to register for the present computer-based weight loss system 10 must have a separate ID code 24 generated from the medical practice of the medical practitioner with whom the patient consulted regarding potential weight loss treatment. Patients may not share the same ID code 24.

With the access ID code 24 in hand, the patient registers on-line with the computer-based weight loss system 10 using the access ID code 24 provided by their medical practitioner. Once registered, the patient is provided with access to various tools of the present computer-based weight loss system 10, including, but not necessarily limited to, information on preparing for surgery and what to expect during surgery, myFoodDiary (that is, a diary focused tool) 28, myStats (that is, a statistic focused tool) 30, myGoals (that is, a goals focused tool) 32, and mySupportNetwork (that is a support network focused tool) 34, all of which will be discussed below in greater detail.

On the day surgery is performed (or after surgery is performed), the patient is provided with a patient ID card 36 granting the patient full access to the computer-based weight loss system 10 of the present invention. Thereafter, the patient may, and is urged to, fully use the complete computer-based weight loss system 10 to enhance his or her recovery and future weight loss based upon the tools provided in conjunction with the computer-based weight loss system 10. As will be appreciated as the computer-based weight loss system 10 is described below in greater detail, this includes updating the patient's profile and utilizing various tools, including, tools designed to assist the patient in continuing to develop personalized eating and fitness plans (myPersonalPlan (that is, a personal planning focused section) 38 and myNutrition (that is, a nutrition focused section) 40), envisioning the new person the patient will become (myProgress (that is, a personal progress focused section) 42), accessing healthy recipes (Recipes) and maintaining a food and diary (myFood Diary) via the myNutrition 40 section, setting up appointments and reminders (myPersonalPlan 38), and developing strategies for meeting personal challenges (myPersonalPlan 38 and myProgess 42).

As discussed above, the present computer-based weight loss system 10 provides both a patient interface 16 and a medical practitioner interface 20. With regard to the patient interface 16, it is initiated with the presentation of a log-in page 43 (see FIG. 4) which leads the patient to a personalized homepage 44 (see FIG. 5) once the log-in is completed. Once logged into the present computer-based weight loss system 10, the patient is provided with access to his or her personalized homepage 44 containing information specifically intended for the patient, as well as general information appropriate for all people taking advantage of the present computer-based weight loss system 10. The homepage 44 is designed to provide quick access to features and functions of the present computer-based weight loss system 10, as well as an overview of the present computer-based weight loss system 10.

More specifically, once the patient has completed the log-in page 43 of the patient interface 16, the patient is directed to his or her personalized homepage 44 providing the patient with access to various tools grouped in sections under the names myPersonalPlan 38, myNutrition 40 (including Recipes 68), What to Expect 130, myFitness (that is, a fitness focused section) 48, and myProgress 42 (including Goals Achieved 50 and Goals in Progress 52). It is contemplated this list of functionalities may expand over time. A variety of linking methodologies are provided in accordance with the patient interface 16 including a tool bar 53 and hyperlinks 55 contained within the main portion of the personalized homepage 44.

Referring now to the myProgress section 42 (see FIGS. 6 to 15), it is employed in a manner allowing patients to celebrate successes, envision the future, track weight loss and record gastric band adjustments. The myProgress section 42 includes links to various tools under the headings Goals Achieved and Goals in Progress (myGoals) 50, 52 (see FIGS. 7 and 8), My Weight Loss (myStats) 54 (see FIG. 9), Band Adjustments (myBandFills (that is, a tool focused upon gastric band adjustment information) 56) (see FIGS. 10 and 11), myPics (that is, a picture focused tool) 58 and theNewMe (that is, a tool allowing a patient to visualize his or her future appearance) 60 (see FIGS. 12 to 15).

In the myGoals tool 32, the patient identifies and focuses on the results that mean the most to him or her. In the myStats tool 30, the patient is able to record their weight and measurements and view a visual representation of their progress to date. With reference to the myBandFills tool 56, filling of the gastric band 22 is recorded and band adjustment surveys are taken. With regard to the myPics tool 58, a plurality of photos is stored, creating a photo journal of the patient's progress as he or she loses weight. Finally, and with regard to theNewMe tool 60, the patient can create virtual images based on height, weight and body type.

When utilizing theNewMe tool 60 of the myProgress section 42, the user is guided through a variety of menus allowing the user to construct a virtual image of their current body type and then adjust the computer generated image body type to create a patient avatar showing how they will look once their weight is reduced via obesity treatment. A virtual image, that is, a patient avatar, of the patient's body is displayed on the myModel tool 62. The patient avatar may be rotated so the patient can see body views from a variety of angles. Included among the many characteristics that may be adjusted in accordance with the present invention are the patient's name, the clothing in which the patient avatar is dressed, the patient avatar's face, the patient avatar's body shape, the patient avatar's height, the patient avatar's weight, the patient avatar's bust size, the patient avatar's waist, as well as various features relating to the eyes, nose and lips. In addition to the input criteria, an adjustment mechanism, including plus and minus buttons is provided for readily adjusting the patient avatar's figure as shown in the exemplary screen (FIGS. 12 to 15).

With reference to the myBandFill tool 56, patients record their band adjustment dates and the amount of saline added or removed from the gastric band 22. In addition, four to six days after the filling of a gastric band 22, patients may complete a band adjustment survey with key questions designed to monitor the effectiveness of each gastric band filling. Depending on the responses given by the patient, the medical practitioner may receive an onTrackAlert (that is, an alert issued in accordance with the present system 10) 64, providing the medical practitioner with feedback regarding the input provided by the patient.

The myProgress section 42 also includes a myPics tool 58 in which the user may upload and display a variety of pictures as his or her weight is reduced during the obesity treatment process.

As the patient treats his or her obesity and loses weight, the patient will be encouraged to establish lifestyle goals. The myGoals tool 32 begins by allowing the user to create specific personal goals, providing access to goals achieved 50 and goals in progress 52. The interface of the myGoals tool 32 provides a dashboard presenting charts, updating the patient's weight, updating the patient's measurements, updating the dress and pant size of the patient, updating medication the patient is taking and updating the patient's goals. The user is then provided with an edit weight and measurement tool 66 in which he or she may input dated information regarding his or her weight on current days and his or her current dress or pant size on current days. This measurement data will calculate total inches lost for the patient. The user may also edit the medications he or she is taking as well as the costs associated therewith. Patients may also be able to record body fat % or lean body mass. In addition to this information being important to a patient, this information is also available to the medical practitioner via the medical practitioner interface 20 and will allow the medical practitioner to actively monitor the patient's progress.

The treatment of obesity is not merely a function of losing weight, but adds to the physical enjoyment of ones life. As such, the myGoals tool 32 provides a mechanism for inputting and editing goals of the user. Finally, the myGoals tool 32 allows the user to create a journal of various input information for his or her review and to see whether he or she is meeting goals set out early in the process. As discussed above, in addition to this information being important to a patient, this information is also available to the medical practitioner and will allow the medical practitioner to actively monitor the patient's progress.

In addition to the myProgress section 42, the patient may also utilize the myNutrition section 40 (see FIGS. 16 to 19). The myNutrition section 40 is intended to provide patients with access to food information and recipe information in a convenient easy to use format.

Figure 17:
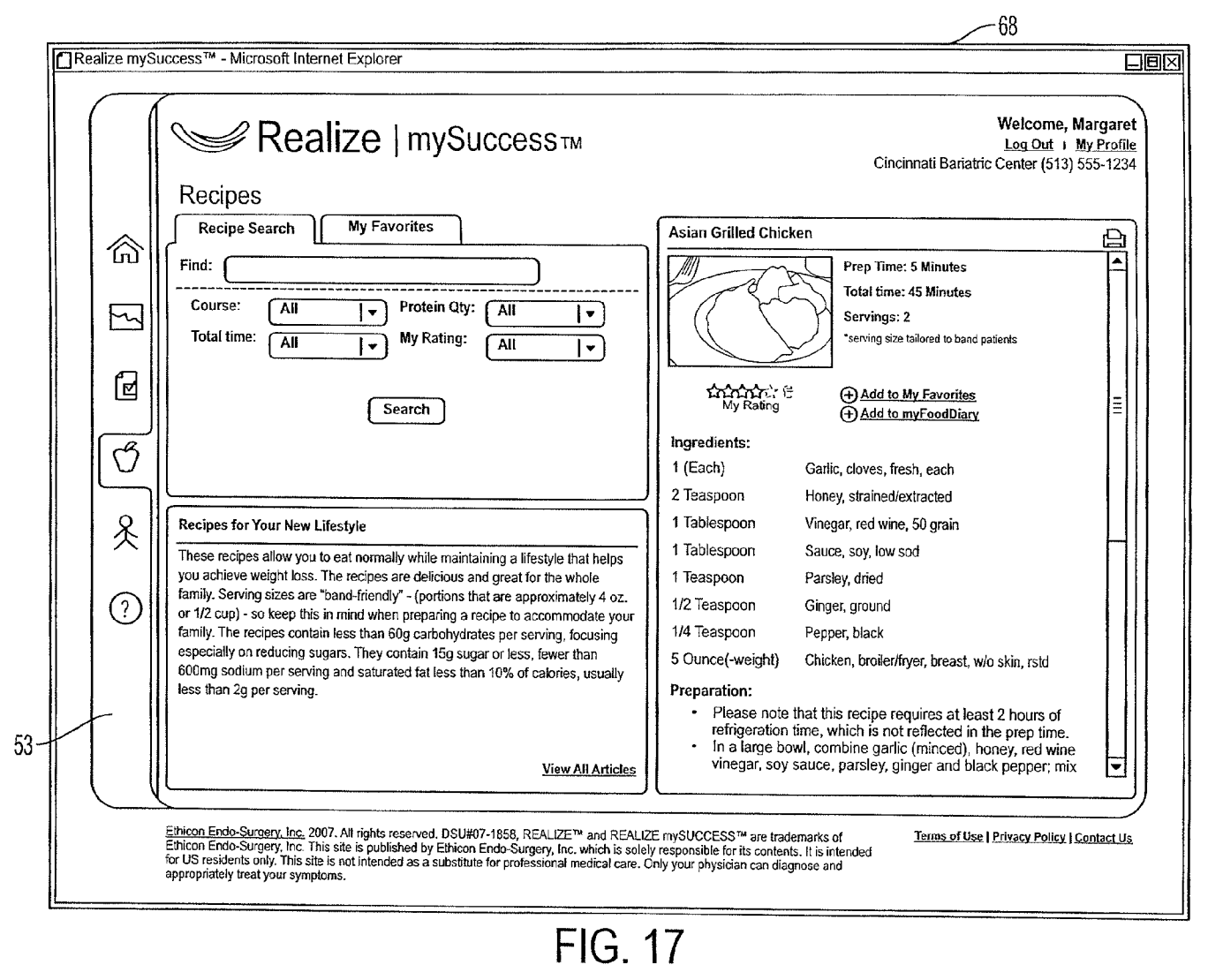

As such, the myNutrition section 40 is divided into two main areas; that is a myFoodDiary tool 28 (see FIGS. 18 and 19) and a Recipes tool (that is, a recipes tool) 68 (see FIG. 17). With the wide variety of choices in the Recipes tool 68 and proactive planning in myFoodDiary tool 28, the myNutrition section 40 provides the powerful combination of information about wholesome foods and healthy habits to last a lifetime. Briefly, and as will be discussed below in greater detail, the myFoodDiary tool 28 allows patients to track what and where they eat, and their mood during meals, their tolerance of a specific food and whether the food was planned or unplanned. Patients are also provided with access to nutritional information on more than 5,000 foods. As to the Recipes tool 68, 400 plus gastric band-friendly recipes are provided for access by users of the present computer-based weight loss system.

The myNutrition section 40 allows the user to gather relevant information regarding various foods he or she may wish to eat. The information relating the foods he or she may wish to eat is readily accessed through the utilization of links to various food types the user may wish to eat, including, information relating to appetizers and snacks, breakfast, lunch, dinner, desserts, meat and poultry, seafood, pasta, fruits and vegetables. In addition, the user may collect favorite recipes for ready access. All of this information is accessed via a series of menus and links, that is, via a tree text search, which quickly and conveniently allows for retrieval of personally oriented information for the patient.

As briefly mentioned above, the patient interface 16 also includes a myFoodDiary tool 28. Research has shown that people who experience long-term weight loss often self monitor with a food diary. In the myFoodDiary tool 28 patients enter what and where they eat, as well as their mood during meals. They also keep track of fluid intake, vitamin/supplement intake, monitor gastric band restriction level and note food tolerance issues. Reviewing information input into the myFoodDiary tool 28 can also help patients identify eating patterns that may sabotage weight loss. For example, seeing the caloric intake 'on paper' helps a patient see where extra calories are coming from (i.e., fluids like mocha coffee or high calorie foods). Patients then see trends and totals that they don't think about unless it is written down.

In accordance with a preferred embodiment of the present invention, myFoodDiary tool 28 allows the individual user to maintain a food log 70. The food log 70 provides a chart showing various nutritional characteristics of the foods eaten by the patient on various days. In accordance with a preferred embodiment, the eaten food is provided in a chart format and includes information relating to how the user felt as he or she ate the food, the location of the meal, the quantity of the various foods eaten and the caloric intake, the fat content of the meal and the protein content of the meal.

As the user eats, updates to the myFoodDiary tool 28 are made easier through the add a food tool 72 that allows users to access food information via the My Favorites tool (that is, a listing of a patient's favorite foods) 74 of the myFoodDiary tool 28. The add a food tool 72 allows the user to readily add various foods to the myFoodDiary tool 28 through the utilization of a search engine by browsing foods maintained on the database, by reviewing a listing of recently eaten foods of the patient, by accessing a listing of foods which the patient has indicated as being favorite foods and/or by using a custom food screen to add foods to the system 10 that are not otherwise listed for ready retrieval by the user. If a food is not found, the user may manually enter a custom food through an input screen allowing for input of information relating to the food, the main nutrients of the food, as well as the vitamin and mineral content of the food. This information is then added to the stored information for subsequent addition to the food log 70. The convenient location and identification of foods for the myFoodDiary tool 28 allows the patient to readily and conveniently add foods to his or her myFoodDiary tool 28.

Figure 18:
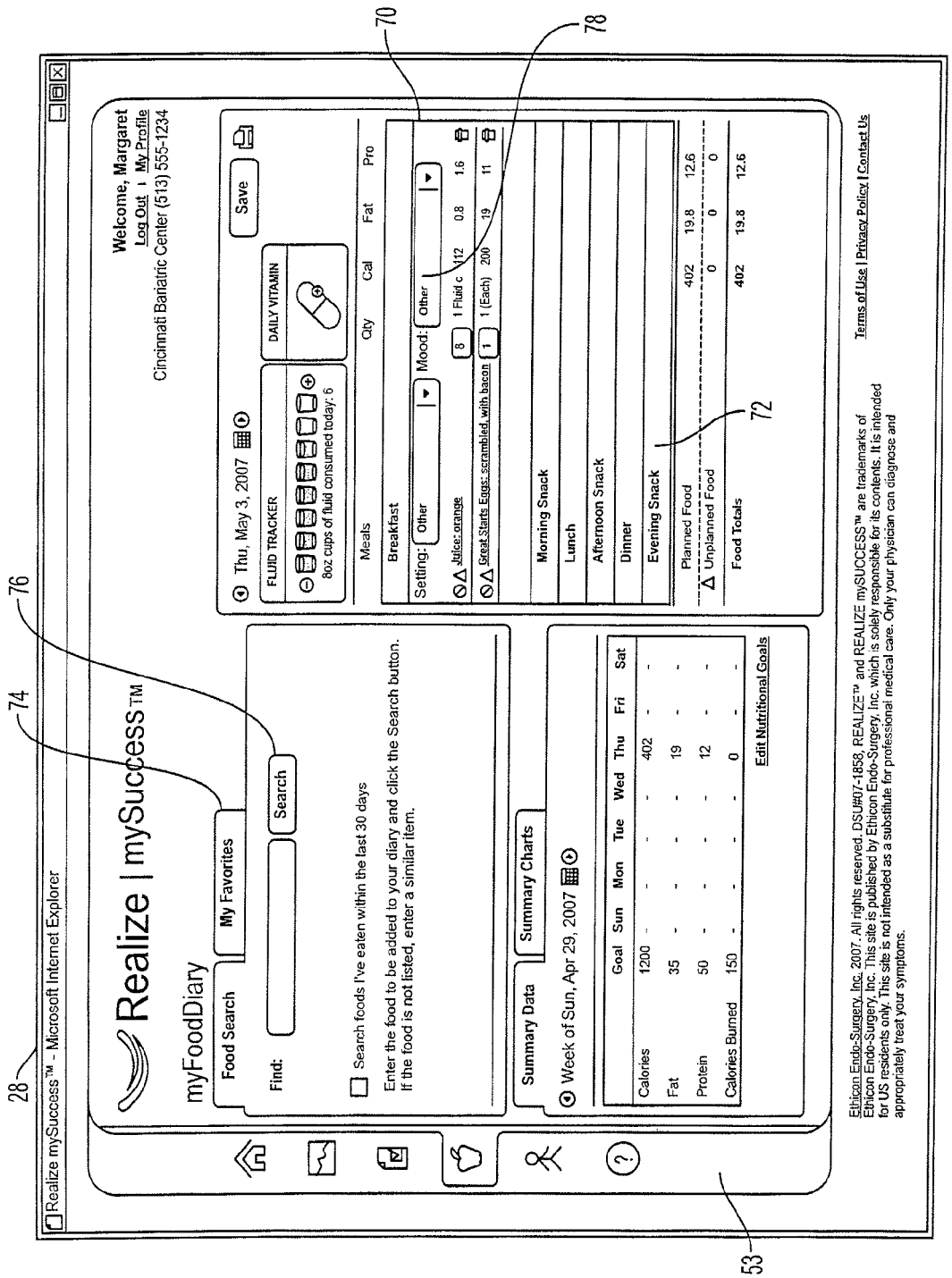
Figure 20:
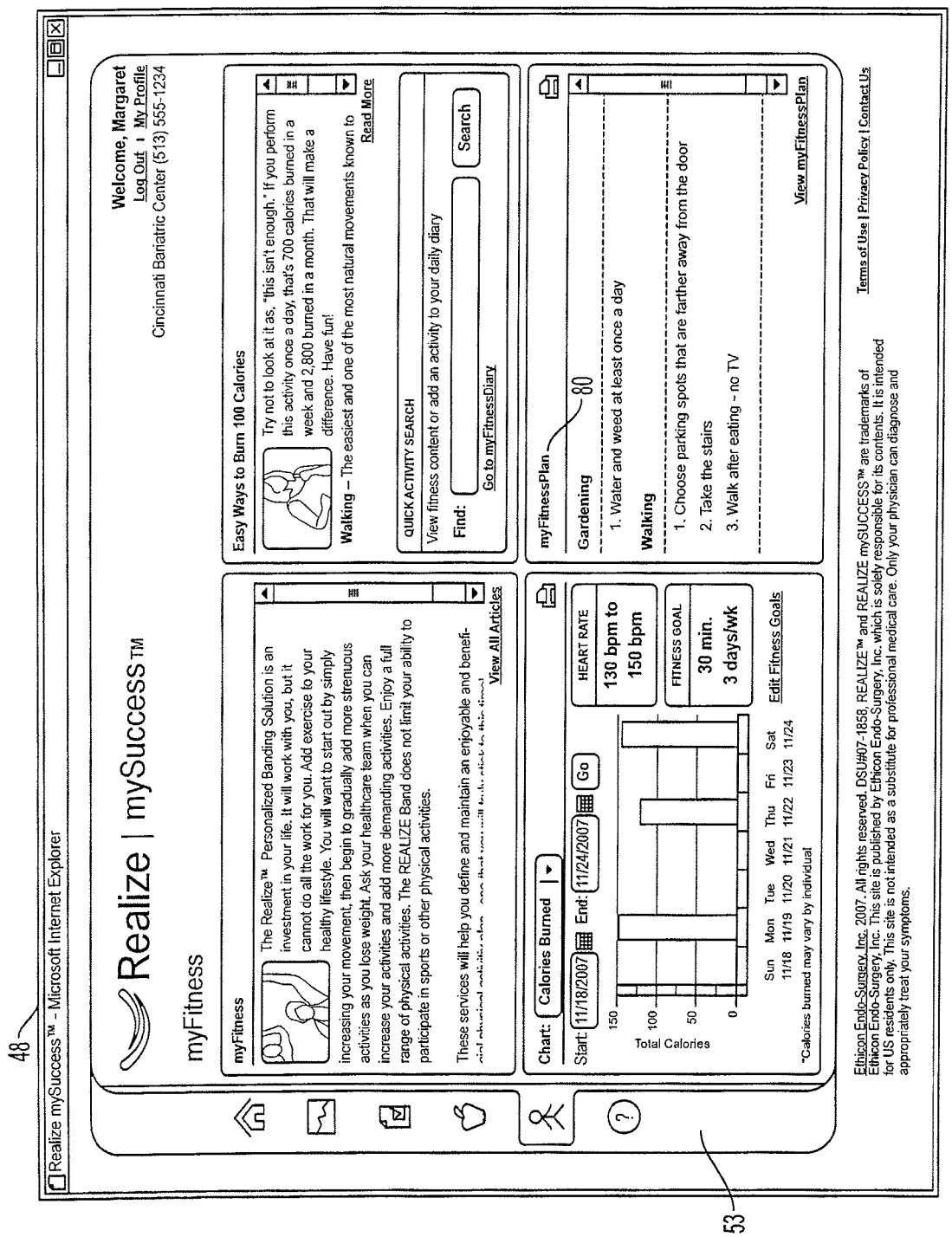
Figure 23:
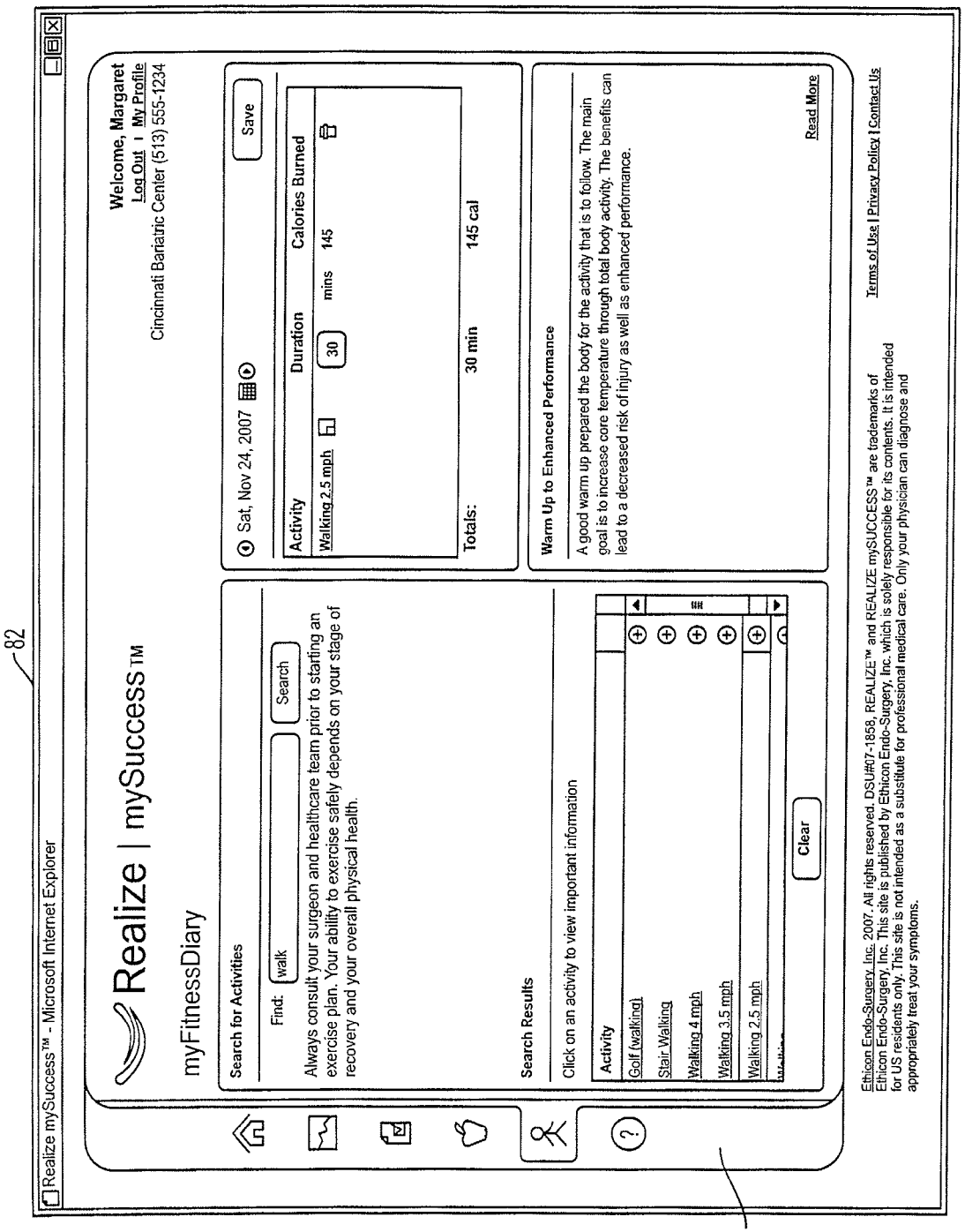
Figure 24:
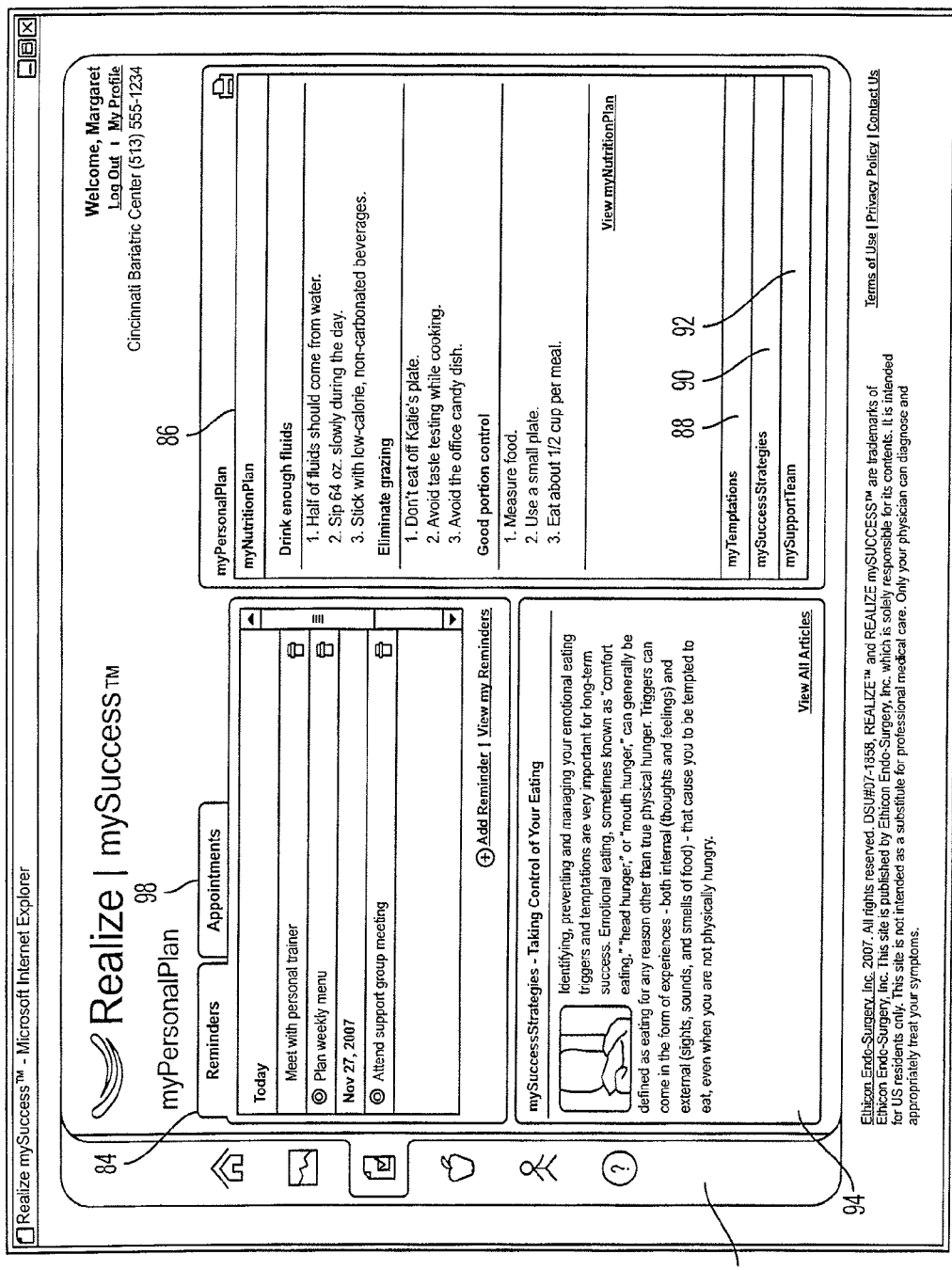
Figure 26:
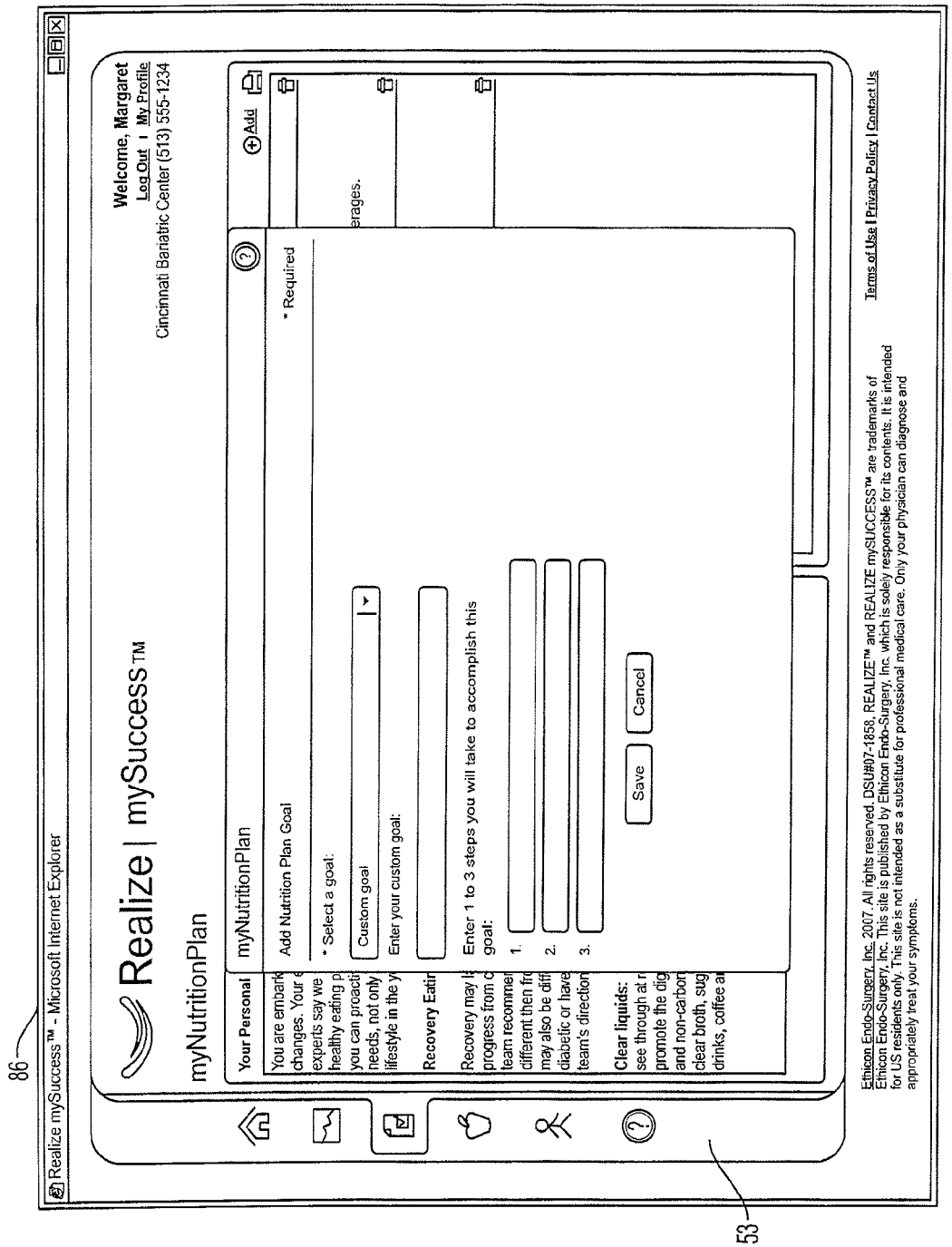
Figure 29:
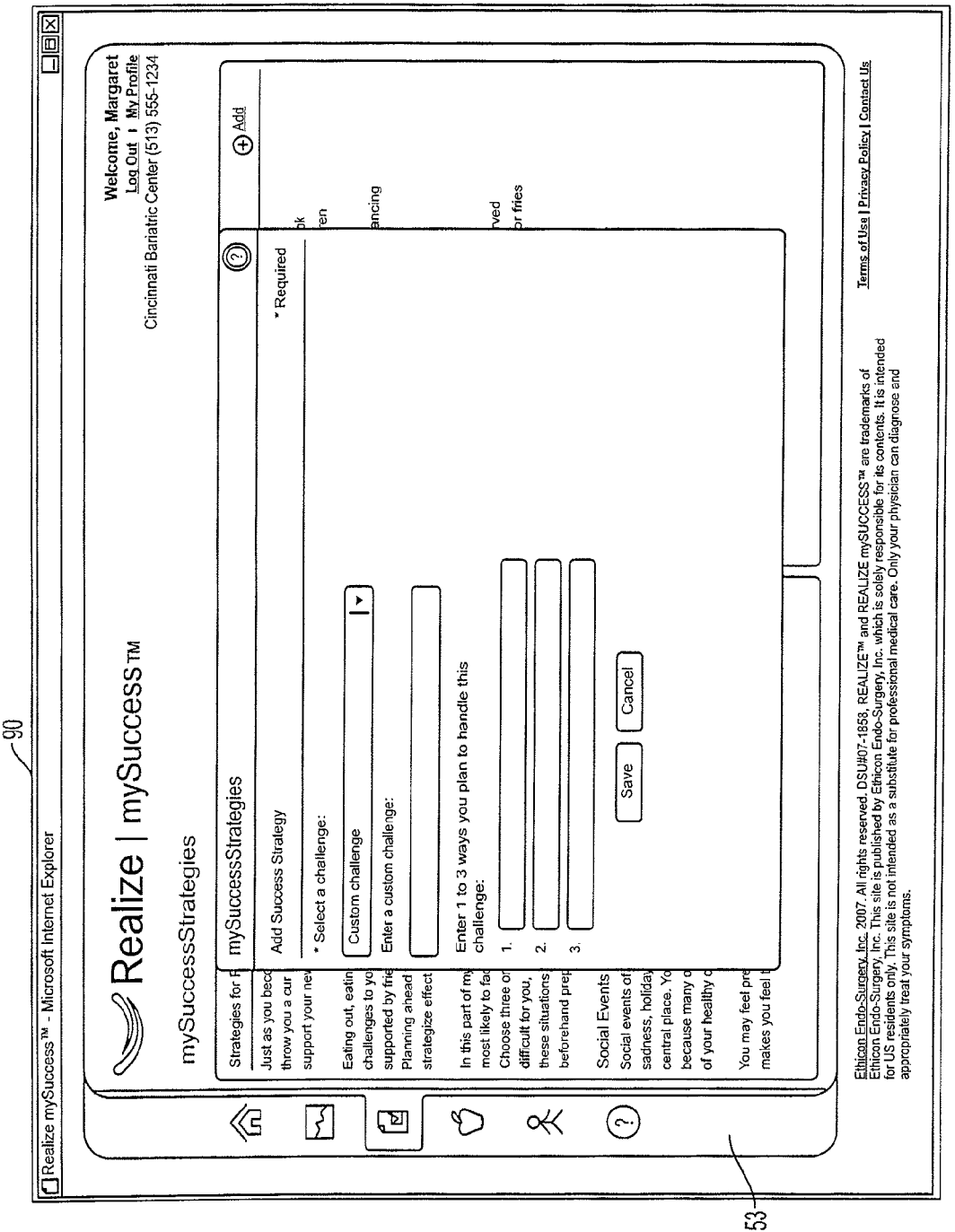
Figure 31:
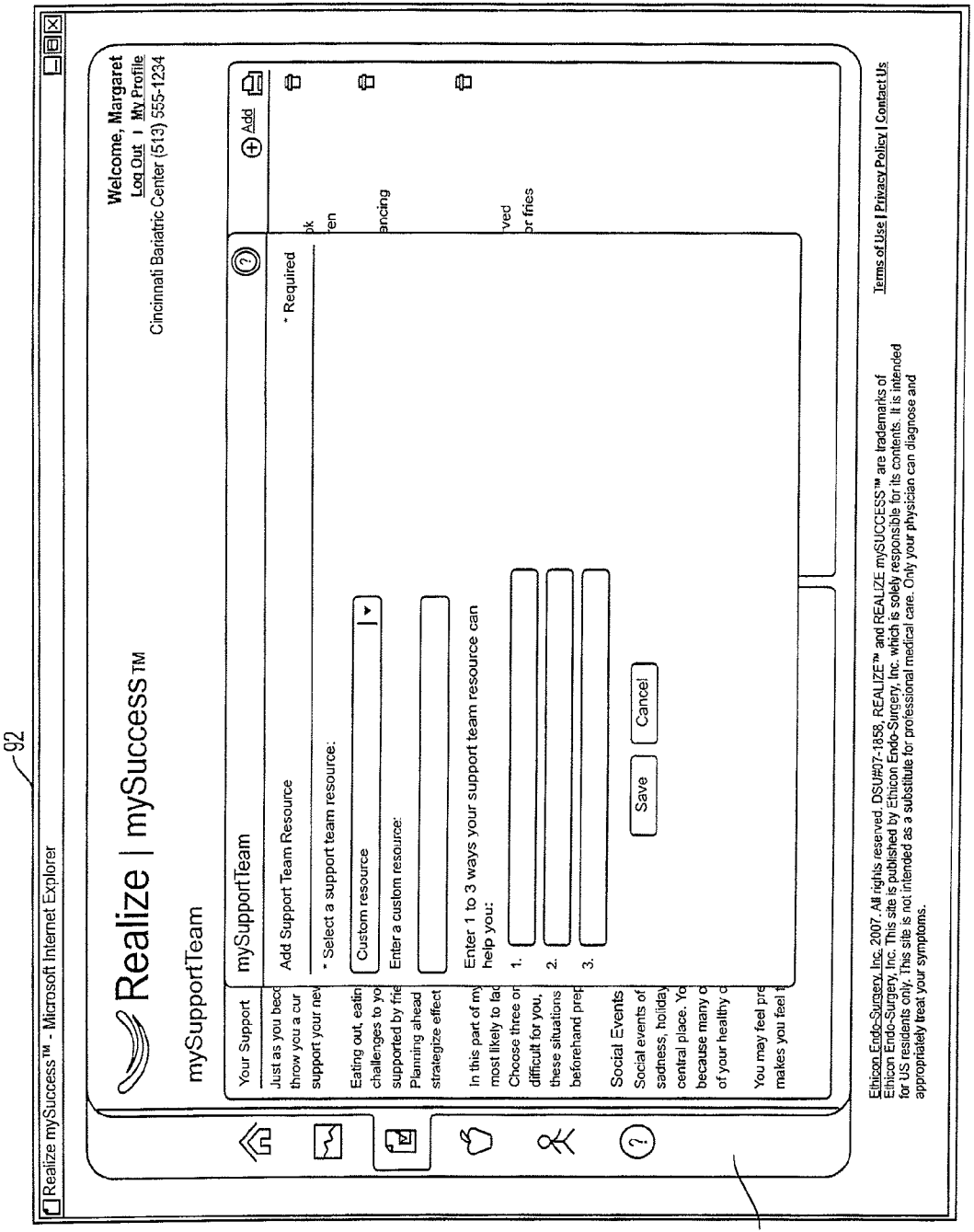
Figure 32:
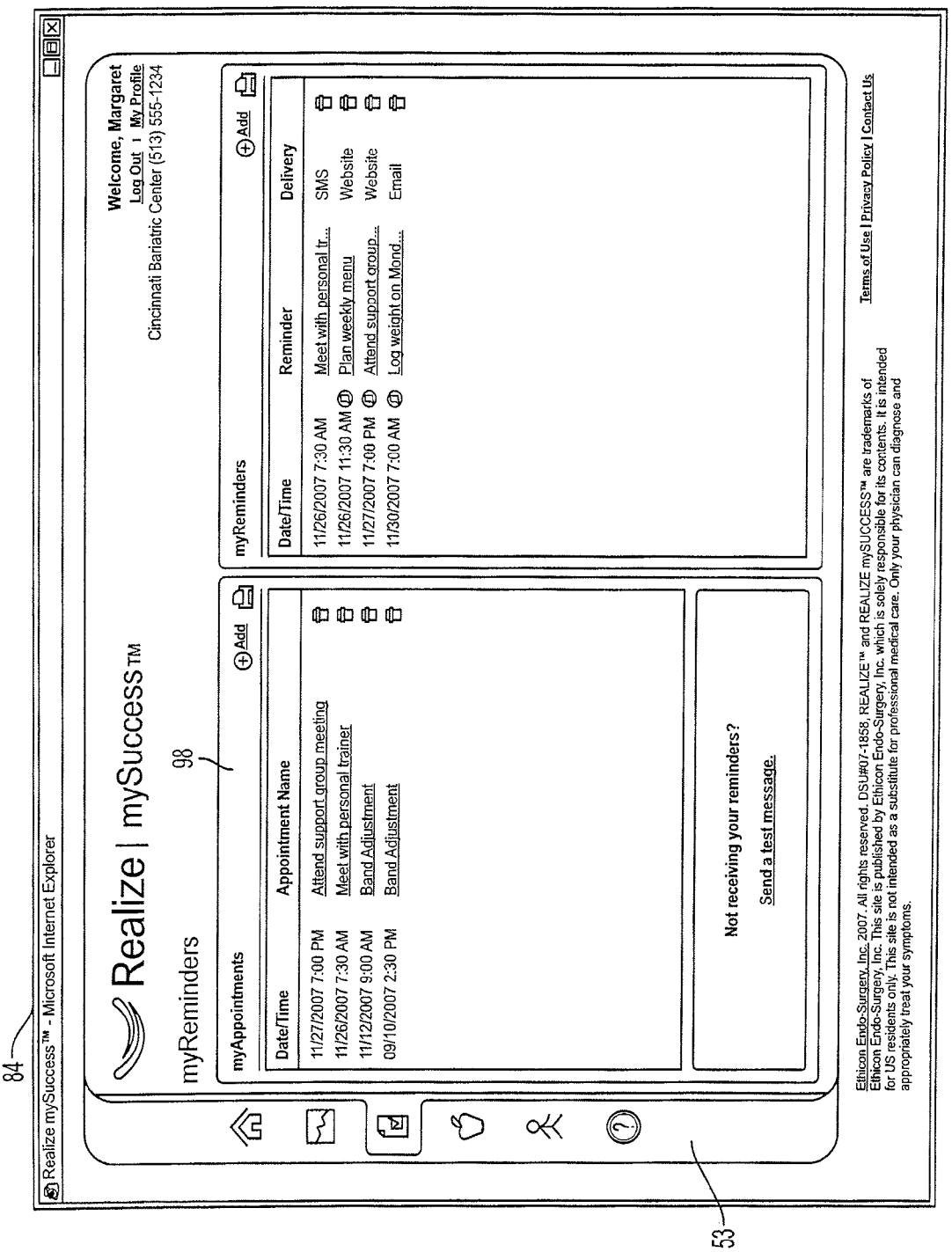
Figure 33:
Figure 34:
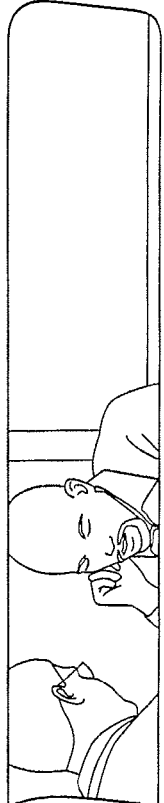
Figure 35:
Figure 36:
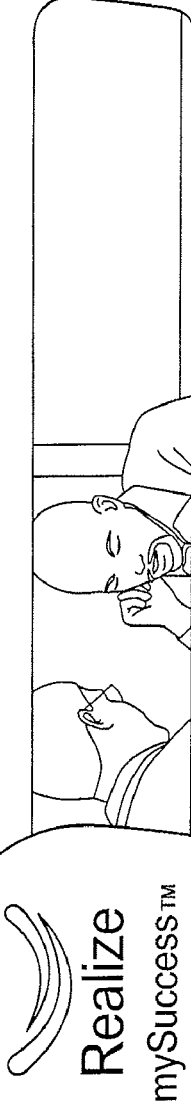
Figure 39:
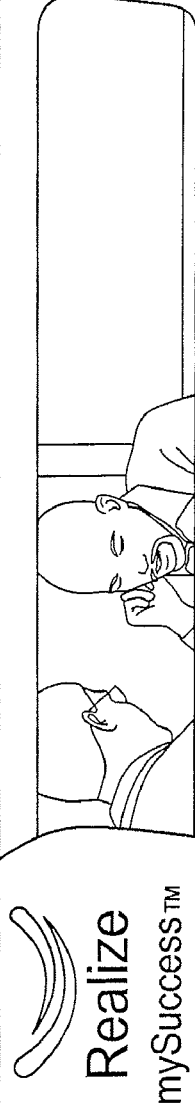
Figure 40:
Figure 42:
Figure 43:
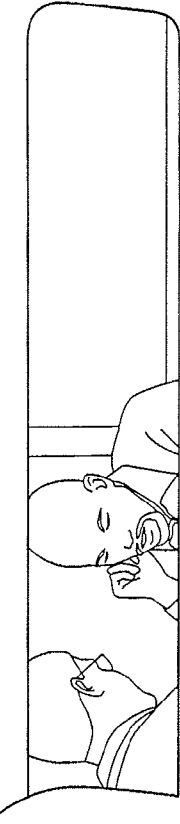
Figure 45:
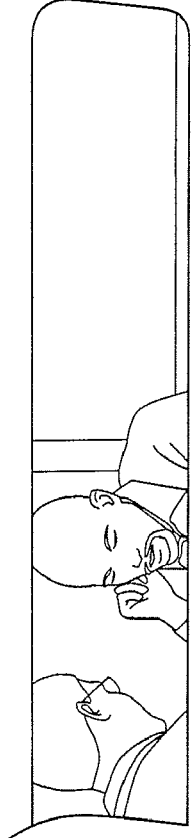

Finally, the myFoodDiary tool 28 allows the user to view charts and graphs of the input information (see FIG. 18). The charts and graphs provide relevant information using various views taking into account such things as caloric intake and the percentage of calories from structured meals. In accordance with a preferred embodiment, the charts and graphs provide summaries of food consumption on a given day, and the interface is provided with drop down menus facilitating the easy entering of dates for consideration. As those skilled in the art will certainly appreciate, the information input through the myFoodDiary tool 28 may be utilized in a variety of ways to create various charts.

For example, dietician/nutritionist annotated recipes (specific preparation techniques to facilitate the tolerance by the patient) are retrieved with nutritional information useful to the patient in making decisions concerning his or her diet. In accordance with a preferred embodiment and with reference to FIG. 19, the recipes are displayed in chart form with information regarding the course for which the recipe is intended, the protein content of the recipe and the calorie content of the recipe. The chart also includes links for adding the recipe to the myFoodDiary tool 28 in the event a patient consumes a meal made from such recipe and would like to add it to the myFoodDiary tool 28. This patient interface 16 also allows users to rate recipes they try and add these recipes to their list of favorite recipes.

The myNutrition section 40 further provides a mechanism for searching various meals. The search mechanism 76 provides drop down menus and keyword searching allowing the user to input various criteria selected from the group consisting of recipe course, main ingredient, dish type, calories per serving, cuisine type, preparation time, average user rating and protein serving. After inputting relevant information, the user is given a list of potential products and/or recipes that fit the criteria set forth in the search terms. The search results may also be used to locate celebrity videos demonstrating the preparation of foods fitting the criteria set forth by the patient. As shown in the various screen shots, the searching feature may be combined with various recipe sections, for example, "Breakfast", so as to focus the search upon a meal of interest. In addition, and in accordance with a preferred embodiment of the present invention, the search results are organized based upon caloric intake, protein content and various other ratings which might make use of the present computer-based weight loss system 10 more beneficial to the patient.

An additional feature of the Recipe tool 68 is the provision of very specific recipes. In addition to the recipes suggested, cooking techniques are also provided. As the user prepares meals suggested through the Recipe tool 68, he or she may add information to the myFoodDiary tool 28 which is discussed below and provides the patient (and medical practitioner) with a convenient way to monitor the patient's food intake. The information may be added through a myFoodDiary input menu 78 that accounts for information such as the date the food was eaten, how the patient felt as they ate the food, the meal setting, the recipe course, the quantity of the food and the serving size. In addition, specified foods, vitamins and fluids may be flagged to indicate an unplanned food or difficulty tolerating certain foods. This information would be used to identify food, vitamin and fluid restrictions as a further diagnostic tool for use in treating patients in accordance with the present computer-based weight loss system 10.

In addition to the provision of various recipes, the myNutrition section 40 also provides web casts from famous chefs. The web casts provide the user with food preparation techniques that may assist in further facilitating the preparation of healthy foods for consumption by patients.

The present computer-based weight loss system 10 also allows for the addition of an activity the user participated in to the myFitness section 48 (see FIGS. 20 to 23). As anyone who has ever attempted to lose weight knows, weight loss is oftentimes based upon a combination of how many calories are eaten and how many calories are used (or burned) in a given time period. As such, by keeping track of the activities in which a patient participates, one may readily keep a thorough log of all relevant activities.

More particularly, the myFitness section 48 helps patients incorporate activities they enjoy into their daily routine. With a variety of options, including traditional exercises (walking, cycling, swimming), as well as everyday activities (cleaning, gardening), each patient can develop a personalized fitness plan. The myFitness section 48 is divided into two main areas; a myFitnessPlan tool (that is, a fitness planning tool) 80 and a myFitnessDiary tool (that is, a fitness diary tool) 82. The myFitnessPlan tool 80 allows patients to track activity sections, including the duration of each activity and the calories burned. The myFitness section 48 may also include exercise programs designed for bariatric patients of varying levels of fitness. The patient may be able to assess their ability to determine the program appropriate for their level of fitness. The myFitnessDiary tool 80 allows access to detailed information regarding each activity (including, but not limited to, muscles used, appropriate form and steps for the exercise, equipment required, pictures and videos).

The present computer-based weight loss system 10 also provides a mechanism for patient planning via the myPersonalPlan section 38 (see FIGS. 24 to 32). One important aspect of obesity treatment involves personal planning as a behavioral modification tool. As such, the Personal Plan section 38 is provided with the patient interface 16. The Personal Plan section 38 allows the user to readily access sections relating to a personal eating plan, taking control of my eating triggers, appointments and reminders, post-operation diet schedule, support networks, handling tough situations and activities under the tool headings of myReminders 84 (see FIG. 32), myNutritionalPlan (that is, a tool providing a guide to proper nutrition) 86 (see FIGS. 24 to 26), myTemptations (that is, a tool focused upon dealing with temptations) 88 (see FIG. 27), mySuccessStrategies (that is, a tool for implementing strategies to successfully achieve goals in accordance with the present system 10) 90 (see FIGS. 28 and 29) and mySupportTeam (that is, a tool providing the patient with ready access to people willing to provide support and encouragement as the patient works to lose weight) 92 (see FIGS. 30 and 31).

As briefly discussed above, the myPersonalPlan section 38 contains a variety of tools that help patients customize their program and proactively plan for success. The five areas of the myPersonalPlan section 38 include a myReminders tool 84, a myNutritionPlan tool 86, a myTemptations tool 88, a mySuccessStrategies tool 90 and a mySupportTeam tool 92. Briefly, and as will be discussed below in greater detail, the myReminders tool 84 allows patients to elect to be notified of appointments and reminded of tasks critical to success by email, text message or at log-in. The myNutritionPlan tool 86 encourages patients to focus on preplanned meals and healthy eating strategies. The myTemptations tool 88 allows patients to identify times they are most apt to eat for reasons other than hunger. The mySuccessStrategies tool 90 allows patients to develop coping strategies for potential stumbling blocks. Finally, the mySupportTeam tool 92 allows patients to identify the family, friends and healthcare providers they rely upon most.

With reference to myNutritionPlan tool 86, myTemptations tool 88, and mySuccessStrategies tool 90, the patient is provided with a mechanism allowing for the input of goals, as well as specific steps, the user will undertake to accomplish in achieving his or her plan. It is contemplated the input goals may be suggested goals or personal goals. For example, and with reference to the myNutritionPlan tool 86, the user will be required to specify steps he or she will take to eat three meals a day, steps he or she will undertake to drink 8 cups of water per day, steps he or she will take to eliminate high fat snacks from his or her diet, and steps he or she will take to ensure daily supplements are taken. The patient will then be reminded of this personal eating plan as he or she moves through the program. This information, as well as the other input information will then be available for the medical practitioner to review and/or edit via the medical practitioner interface 20 as discussed below in greater detail.

As most people will appreciate, eating is often triggered by various external influences. As such, and with reference to the myTemptations tool 88, and the mySuccessStrategies tool 90, the user will take steps to identify his or her eating triggers and specify ways in which he or she may address these eating triggers. For example, the user may specify how he or she will deal when confronted with anxiety, boredom, work related events and activities. As with the goals for eating properly, the user (and medical practitioner) will be regularly provided with reminders of the ways in which he or she can reach preestablished goals.

Referring to the myReminders tool 84, appointments and reminders are selectively input through a convenient interface composed of various menus from which the user can select for inputting information. The appointments and reminders can then be retrieved by the patient for use in complying with the obesity treatment program. In accordance with a preferred embodiment of the present invention, the appointment and reminders are organized and issued to the patient in a manner specifically designed to address the patient's needs depending upon the stage of obesity treatment in which the patient is participating.

The diet plan of the user is also presented in a convenient, straight forward manner so the user may understand what foods are to be eaten on which days. For example, and as discussed below in greater detail, where a postoperative diet schedule is provided, the user will initially consume only clear liquids, then move on to all liquids, then move on to pureed foods and finally, move back to solid foods.

In addition to other support mechanisms and content provided by the Personal Plan section 38, the Personal Plan section 38 may also provide post-operation wound care information 94 and post-operative diet schedule 96. It should be understood this information may be available outside of the Personal Plan section 38. This allows the patient to access information for assisting in the physical recovery process. As will be discussed below with regard to the medical practitioner interface 20, this information will cover both general information and patient specific information input by the medical practitioner.

People also are readily aware that support is important to achieving any goal. As such, the user may indicate various support resources which will be readily available for access by the patient to assist him or her in dealing with obesity.

The user will also be presented with a mechanism for handling tough situations via the myTemptations tool 88, the mySuccessStrategies tool 90 and the mySupportTeam tool 92. This will be achieved by allowing the user to input how he or she will handle various events. For example, using the mySuccessStrategies tool 90 the user will be required to identify how he or she will host or attend a party or a sporting event where chips and snacks are available; attend a birthday party where unhealthy desserts are served; go out with a group of friends who might stop by a fast food restaurant on the way home; stop at a local coffee shop in the morning where high calorie sugar filled drinks are served; deal with a cookout where hamburgers, hotdogs and other high fat foods are served; and/or deal with situations where doughnuts, pastries and bagels are left out in a shared dining area at work.

Finally, the myPersonalPlan section 38 provides a scheduled Reminder tool 98. The scheduled Reminder tool 98 includes a mechanism for viewing all reminders. These reminders may be input by the patient, come from the medical practitioner as he or she monitors the patient's progress or from preset system alerts relating to the condition and data input of the patient. In particular, the system algorithm sends onTrackAlerts to patients based upon specific data patterns identified by the central server 12. For example, reminders are not sent through system algorithm. Only onTrackAlerts are sent through system algorithm. Reminders are only sent via patient request or practice inputs.

In addition, the scheduled Reminders tool 98 includes an interface for adding reminders. The addition of reminders is achieved via an interface composed of input sections combined with drop down menus. As such, it is very easy for a user to input various reminders that he or she would like to view during the course of the obesity treatment. The scheduled Reminders tool 98 also allows the user to view reminders by week or other information. Reminders may be received via email, text messaging, telephone or any other mechanism desired by a user.

It is contemplated a journal may be added to the patient interface for recording thoughts, feelings and notes of the day. The journal would also combine the notes with other relevant information for that day (i.e., exercise notes, weight, food diary entry, etc.) to provide a complete set of information at a glance. It is contemplated a system of rewards and recognitions may be added that will encourage, motivate and allow the patient to achieve "levels" or attain "rewards" for doing specific activities in the site such as logging their weight weekly. The ability to compete with other users or form "teams" based on achieving "levels" may also be added.

The present system provides information to the patient based on the surgery stage of the patient (i.e., pre-op, post-op 0-1 week, post-op 1-3 weeks, post-op 4-6 weeks, beyond, etc.). This content is also available at any stage in the Help section of the site. There is also an audio help feature in the site to provide overviews of the site and the features within the site.

As discussed above, the present computer-based weight loss system 10 also provides a medical practitioner interface 20. The medical practitioner interface 20 first includes a medical practice homepage 100, or practice dashboard, where the medical practitioner is provided with practice statistics and navigation tools.

Each time a medical practitioner logs onto (see FIG. 33) the medical practitioner interface 20, the homepage 100 (see FIG. 34) will display up to date statistics regarding patients and their use of the present computer-based weight loss system 10. The statistics provided may include information on patient registration, onTrack Alerts, frequency of use, and how many pounds patients have lost using the surgical weight loss (or other bariatric) procedure. From the practice homepage 100, and as will be discussed below in greater detail, a variety of tools are readily accessed.

The readily available patient information may include information regarding patient weight history, patient information (i.e., surgery data, surgeon, etc.), patient log-ins to the system 10 and completion of a personal plan by the patient. The medical practitioner interface 20 provides the medical practitioner with access to tools relating to a patient's food diary 28, onTrack Alerts 64, gastric band adjustment 56 and patient activity levels 80, 82.

The medical practitioner interface 20 further includes a mechanism for patient management 102 (see FIGS. 36 to 41). This portion of the medical practitioner interface 20 provides users with an overview of each patient, food, weight, adjustments, alerts and exercise diary for each patient, a listing of patient reminders, a listing of patient plans, and a listing of lifestyle goals. Currently, all of this information is put in by the patient via the patient interface 16 as discussed above. However, it is contemplated such information may be input by the medical practitioner. The patient management section 102 further provides charts allowing the medical practitioner to readily monitor and/or edit the information input by the patient and/or by the medical practitioner (as contemplated in accordance with the present invention).

The medical practitioner interface 20 is also provided with a user administration section 124 (see FIG. 43) designed to allow the practice administrator to set up the medical practitioner interface 20 for the specific use of the medical practice. The user administration section 124 also provides for system set up allowing the medical practitioner to input appointment information and appointment recurrence options. The system set up also allows the medical practitioner to initiate first band-fill appointment, support group meetings, monthly check-ins and semi-annual check-ins. The personal plan editor also allows the medical practitioner to input and edit a personal eating plan, a mechanism for controlling eating triggers, an appointment and reminders section, a postoperative diet schedule, a postoperative wound care schedule, a support network and a situation for handling tough situations.

The medical practitioner interface 20 is further provided with a newsletter editor. This allows the medical practitioner to create a newsletter from which the patients may receive information regarding their treatment.

In accordance with a preferred embodiment of the present invention, the practice homepage 100 of the medical practitioner interface 20 includes links to onTrackAlerts 64, new Patient Codes 116, myPatients 118, Patient Content 120, Using REALIZE MYSUCCESS (that is, the present computer-based weight loss system 10) 122, User Administration 124 and HELP 126. Each of these areas can be accessed through appropriate links located on the left side of each main page. The last link "HELP" 126 provides access to frequently asked questions. Referring to the Using REALIZE MYSUCCESS section 122 (see FIGS. 44 and 45), this section provides links to informative articles on features and functions, as well as tips on how to integrate the present computer-based weight loss system 10 into patient care.

The medical practitioner interface 20 provides an alert mechanism for use by the medical practitioner. In accordance with a preferred embodiment of the present invention, this tool is the onTrackAlert tool 64 of the present computer-based weight loss system 10. In particular, when potential problems are identified, an alert tool, that is the onTrackAlert tool 64 (see FIG. 46) of the present computer-based weight loss system 10 is activated. The onTrackAlert tool 64 allows medical practitioners to identify issues they may want to address with their patients. These alerts may include weight gain or plateaus, medication reviews, gastric band adjustment survey information, and whether patients are utilizing the present computer-based weight loss system 10 on a regular basis. The onTrackAlerts are displayed by type and are searchable using drop-down menus at the top of each screen. To review a suggested course of action, the medical practitioner need only click the suggestion link following each onTrackAlert. At this time, detailed patient information is accessed by clicking a patient's name. The practice may contact the patient directly or electronically through the site interface.

By catching problem periods early, the patient can be redirected on the path to success. The following list indicates various onTrackAlerts contemplated for use in accordance with implementation of the present invention and what each onTrackAlert means and offers some possible actions to take.

Band Adjustment Survey: This onTrackAlert is issued when a patient response in the band adjustment survey indicates another band adjustment may be warranted. The survey is made available to the patient four days after a patient-entered gastric band adjustment appointment. The survey consists of four yes/no questions:
  1. Do you feel your restriction is giving you a feeling of fullness after eating?
  2. Were you able to progress back to a regular meal without difficulty?
  3. Are you experiencing any significant events when eating (vomiting, unable to swallow, excessive productive burping, etc.)?
  4. Have you noticed any serious reflux, pain when eating or recurrent or frequent reflux or vomiting?
    If the patient answers "no" to either of the first two questions, or "yes" to the third or fourth questions, an onTrackAlert is sent to the medical practitioner.
  Suggestion: Check the chart and decide if the patient should be seen before the next scheduled appointment.
Twenty-five pound weight loss increments: This onTrackAlert notifies the medical practitioner every time a patient loses 25 pounds. The specific onTrackAlert will let the medical practitioner know the cumulative weight loss from the patient's starting weight. (i.e., OnTrackAlerts are issued, for example, after a patient loses 25 lbs, 50 lbs, 75 lbs, etc.)

Suggestion: Check or adjust medication levels for those medications the medical practitioner is prescribing or refer the patient to the prescribing physician for evaluation.

Three-week weight gain: This onTrackAlert indicates that over the past three weeks, a patient has reported at least a seven-pound weight gain.

Suggestion: Contact the patient or schedule an early appointment to diagnose the reason for the gain. Intervene as indicated with a gastric band adjustment, a request for the patient's food diary, or an appointment with the nutritionist or mental health practitioner.

Four-week weight plateau: This onTrackAlert lets the medical practitioner know that a patient has stopped losing weight and is within plus or minus two pounds of the weight entered 28 days ago.

Suggestion: Contact the patient or schedule an early appointment to diagnose the reason for the plateau. Intervene with a gastric band adjustment, a request for the patient's food diary, or an appointment with the nutritionist or mental health practitioner.

No band adjustment eight weeks after surgery: This onTrackAlert is triggered when a patient has not entered a gastric band adjustment 56 days after the surgery date. Either the patient has failed to have a gastric band adjustment or he or she has not entered data from the appointment into his or her record.

Suggestion: Check the medical practitioner records to see if the appointment has occurred. If not, remind the patient of the importance of the gastric band adjustment process and schedule an appointment. If he or she has had a gastric band adjustment, remind the patient to enter the data as part of taking personal control of his or her weight loss process.

Changed practice affiliation: This onTrackAlert lets the medical practitioner know that a patient has indicated he or she is no longer associated with the practice of the medical practitioner. This is initiated either when the patient dissociates from a medical practitioner's medical practice or enters a Surgeon's Practice ID code from a new medical practice.

Suggestion: Contact patient to verify the change and reduce the incidence of "lost patients" in the medical practitioner's practice statistics.

No logged weight for two weeks: This onTrackAlert occurs when the patient has not entered a weight for 14 days, even though he or she has logged onto the present computer-based weight loss system 10.

Suggestion: Call the patient to stress the importance of weekly weight entry as part of monitoring progress between office visits.

No logged site access for four weeks: This onTrackAlert indicates that the patient has not logged into the present computer-based weight loss system 10 for 28 days.

Suggestion: Call the patient to understand why he or she is no longer using the resources provided.

As discussed above, the present computer-based weight loss system 10 includes an onTrackAlerts tool 64. The onTrackAlerts tool 64 provides pertinent information that enables the medical practitioner to track patient progress, address issues as they arise, and integrate care between appointments. The onTrackAlerts tool 64 also serves to extend the presence of the medical practice and the expertise of the medical practitioners into the patient's everyday life, reinforcing the feeling of supportive relationship. The present computer-based weight loss system 10 provides patients with a structured approach to compliance and behavior modification. Moreover, it saves medical practice time and effort by focusing a medical practitioner's attention on patients who need help the most.

The myPatients section 118 of the medical practitioner interface 20 provides a list of patients who have opted to share their information with the medical practice. The list of patients may be sorted by patient name, surgery date, surgeon and last log-in by clicking by an appropriate column title. The patient list can also be browsed alphabetically, using the letter links above the list. A particular last name may be searched for using the text box and clicking search. In addition, a patient's name may be clicked upon to reveal complete details.

When a medical practitioner clicks on a patient's name, basic information and weight history are displayed by default. There are links to access the patient's food diary, band adjustments and onTrackAlerts. This page of the myPatients section 118 also provides options to disassociate a patient from your medical practice. However, if a medical practitioner disassociates from a patient, the medical practitioner will no longer receive the patient's onTrackAlerts or have access to any of the patient's input information. The patient cannot be reactivated by the medical practice. If the medical practitioner wishes to begin receiving onTrackAlerts again or to access the patient's data, the patient needs to be re-associated with the medical practice by entering a surgeon's practice ID code 24 on his or her user profile. In addition and with reference to another portion of the myPatients section 118, a screen displays a snapshot of the patient's food diary. The food diary displays what was eaten, including details on calories, fat, protein, tolerance issues and whether eating the food was planned or unplanned. By reviewing a patient's food diaries, the medical practitioner can help the patient identify problem areas and suggest nutritious alternatives. In accordance with a preferred embodiment, a daily view of the food diary is shown by default. However, a weekly view may also be shown by simply clicking upon an appropriate link. In addition, different days of the food diary may be displayed by simply clicking on date links.

The myPatients section 118 also provides a gastric band adjustment screen 128 that displays patient entered data regarding gastric band adjustment dates, the amount of saline added or removed, the calculated cumulative fill amount, and band adjustment survey date and results. This information allows the medical practitioner to monitor patient reaction to gastric band adjustments, even when the responses to survey questions may not trigger an onTrackAlert. As those skilled in the art should appreciate, the patient entered data may or may not be consistent with the clinical records maintained by a medical practitioner.

As discussed above, an onTrackAlerts tool 64 is also provided by the present computer-based weight loss system 10. The onTrackAlerts tool 64 may be reviewed for particular patients. Reviewing onTrackAlerts can assist the medical practitioner in identifying specific areas to target for behavior modification. The information can be sorted by alert type or alert date by simply clicking on an appropriate column title.

In addition, the medical practitioner interface 20 also allows the medical practitioner to identify articles for review by patients. If the medical practitioner would like to identify articles related to the health and wellness of the patient, the patient may review the content available from his or her homepage 44, myProgress page 42, myPersonalPlan page 38, myNutrition page 40 or myFitness page 48 by clicking on an appropriate link.

As briefly discussed above, the medical practitioner interface 20 also includes a User Administration section 124. The User Administration section 124 serves as an access point for experts within the office. These experts may be responsible for establishing and maintaining user accounts. As a result, the User Administration section 124 allows the administrator to create a new user by entering all requested information at the bottom of the screen and clicking create new user. The User Administration section 124 also allows an administrator to grant access to different areas of the computer-based weight loss system 10 using patient information, user administration information, code generation, and all site features check boxes. The User Administration section 124 also allows the administrator to delete a user, or edit a user's name by clicking the appropriate link in the actions column; change a user's password, using the change password link in the password column; and save the changes through the utilization of the save changes button.

The tools provided by the present computer-based weight loss system 10 are designed to accelerate patient progress in adjusting their lifestyle to support weight loss goals after surgery. It is also designed to help healthcare professionals use their time with patients to focus quickly on areas where they could use some additional support. Medical practitioners will integrate the present computer-based weight loss system 10 into their current professional practice and, over time, find ways to use its features to increase patient success.

To get started, the following are suggested implementations leveraging the benefits of the present computer-based weight loss system 10 as a medical practitioner interacts with patients in various settings.

During preoperative dietary consultations the medical practitioner should: ask patients to maintain their myFoodDiary 28 on the present computer-based weight loss system 10 prior to surgery; review the analyzed myFoodDiary 28 with the patient (as with any food diary); review data on meal settings, moods, and the planned or unplanned nature of meals to help patients identify possible areas for improvement; and/or identify any particular areas they should address postoperatively when they build the myPersonalPlan section 38.

During the first appointment after surgery the medical practitioner should: make sure patients have their Patient Card ID 36 for the present computer-based weight loss system 10 as it relates to their gastric band; ask if they have successfully logged on to the present computer-based weight loss system 10; remind patients to complete the areas in the myPersonalPlan section 38; and/or emphasize the importance of entering weekly weights on the present computer-based weight loss system 10.

During gastric band adjustment appointments or nurse visits the medical practitioner should: review weekly weight charts with patients and help identify any patterns; remind patients to complete and continually review their specific actions and plans in the myPersonalPlan section 38; suggest the use of patient entered alerts to help stay on track; emphasize the importance of entering weekly weights on the present computer-based weight loss system 10 under the myStats tool 30; ask them about any onTrackAlerts they have received and reinforce the importance of taking action on them; when gastric band adjustments are made, remind patients of the importance of completing the Band Adjustment Survey when it appears four days after the gastric band fill; and/or also see suggestions below on exercise and psychological consultations. If the medical practitioners medical practice does not have these specialists on staff, consider if a referral would be helpful.

When a patient hits a plateau or gains weight the medical practitioner should: ask patients to keep a food diary using the myFoodDiary tool 28; ask patients to identify any patterns in entries to the myFoodDiary tool 28, including food choices, times, settings and moods when eating; reinforce the need to plan meals; review weekly weight charts with patients; identify and discuss any different behaviors that were in place when weight loss was successful; ask patients to review areas in the myPersonalPlan section 38 and ask if they are executing the plans (if so, work alternative plans; if not, ask how they will get back on track); and/or suggest patient entered alerts and reminders to help stay on track.

During postoperative dietary consultation the medical practitioner should: ask patients to keep their food diary (myFoodDiary 28) on the present computer-based weight loss system 10; do the medical practitioner's usual review of myFoodDiary data; review any foods flagged as tolerance issues and provide guidance on evaluating tolerance issues and introducing new foods into a patient's menus; review the setting, moods, and planned/unplanned data to help patients identify possible areas for improvement; review patients' plans for maintaining their new lifestyle in the myNutritionPlan tool 86, mySuccessStrategies tool 90 and myTemptations tool 88; ask if they have found themselves in one of the situations listed in their plans; ask if patients are using the Recipes tools 68; remind patients to look for healthful recipes on the present computer-based weight loss system 10 and be sure to check portion sizes; and/or ask how the present computer-based weight loss system 10 is helping them.

Postoperative psychological consultation should include the following: ask patients to bring along personal plans for professional review and guidance by the medical practitioner; ask patients to review progress on the goals set in the myGoals tool 32; discuss plans patients have created in the myTemptations tool 88 and mySuccessStrategies tool 90; help patients connect myPersonalPlan section 38 entries with goal accomplishment; use myPersonalPlan section 38 information to discuss whether problem areas arise from insufficient planning or inadequate execution; ask what they have learned about themselves by using the present computer-based weight loss system 10 since their last visit.

In suggesting support groups for patients undergoing weight loss in accordance with the present computer-based weight loss system 10 the medical practitioner should: remind patients to log weight weekly; ask patients to bring copies of their personal plans to the support group to note any new ideas on areas they are working on and to share ideas with others; ask patients to report successes on the goals they set in the present computer-based weight loss system 10; and/or remind them to review the materials on the present computer-based weight loss system 10 and update any plans based on new learning in the support group.

During exercise physiologist visits the medical practitioner should: encourage patients to increase activities using the myFitnessPlan tool 80. If they already have a plan, assess their execution of the plan; encourage patients to use the myFitnessDiary tool 82 to log fitness activities and to track progress. Evaluate myFitnessDiary 82 entries compared to myFitnessPlan tool 80; for patients who are not yet as active as needed, suggest they look through the 50+ possible activities listed to find appropriate activities that fit their lifestyle.

The present computer-based weight loss system 10 helps patients establish a tailored plan to develop new, healthy habits in the areas of physical activity, nutrition, and emotional wellbeing. Through utilization of the present computer-based weight loss system 10, medical practitioners and patients can set goals and continuously monitor their progress, especially for the first three years as they adjust to their new gastric band lifestyle. The present system also allows users to apply the data to query for reports and research purposes.

In addition, it is contemplated that the present system will be modified to provide for the ability to send and receive data from the central server via a mobile device or desktop application. For example, this will allow one to log their weight via mobile phone such as, cell phones, personal digital assistants, etc. In addition, patients may receive an SMS (short message service) and they input their weight into the site using this interface. In addition, the present system may provide a reward feature wherein patients are provided with rewards or points for compliance with utilization of the site. The points would serve as a competition or incentive to incorporate the behavior modification features of the present invention into their lives. The system further provides for mapping (or grouping) people to create a spirit of teamwork and/or competition. This will support and challenge individuals using the system as they work together toward a common goal. The present invention also provides the ability for information to be transmitted from the gastric band to the server via a mobile device.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A computer-based weight loss system for supporting bariatric treatment of obesity that is accessible to both the patient and the medical practitioner, comprising:
   a central server maintaining a library of information related to the treatment of obesity;
   a patient interface linked to the central server, wherein the patient interface provides for uploading and downloading of information to the central server, the uploaded information is processed by the central server and then made available to the medical practitioner and the patient, the patient interface also providing access to information selected from the group consisting of bariatric care pathway, behavioral modification planning, fitness, preoperative diet, postoperative diet, monitoring of a gastric band, monitoring of a patient's weight, monitoring caloric intake, nutritional information.

2. The computer-based weight loss system according to claim 1, further including a medical practitioner interface linked to the central server, wherein the medical practitioner interface provides for uploading and downloading of information to the central server, the uploaded information is processed by the central server and then made available to the medical practitioner and the patient.

3. The computer-based weight loss system according to claim 2, wherein the central server integrates information from a plurality of medical practices.

4. The computer-based weight loss system according to claim 2, wherein the computer-based weight loss system generates data alert to the patient and medical practitioners via the respective patient interface and the medical practitioner interface.

5. The computer-based weight loss system according to claim 2, wherein the medical practitioner interface also provides a means for the medical practitioner to retrieve, edit and control information uploaded by the patient.

6. The computer-based weight loss system according to claim 2, wherein the patient interface includes tools selected from the group consisting of tools designed to assist the patient in continuing to develop personalized eating and fitness plans, tools designed for envisioning the new person the patient will become, tools allowing access to healthy recipes, tools for setting up appointments and reminders, and tools for developing strategies for meeting personal challenges.

7. The computer-based weight loss system according to claim 2, wherein the patient interface includes a homepage and the homepage provides the user with access to tools respectively grouped in a personal plan focused section, a nutrition focused section, a fitness focused section, and a progress focused section relating to a patient's weight.

8. The computer-based weight loss system according to claim 7, wherein the progress focused section includes a tool allowing the patient to identify and focus on results that mean the most to him or her, a tool allowing the patient to record his or her weight and measurements and view a visual representation of his or her progress to date, a tool allowing the patient to record filling of his or her gastric band and participate in band adjustment surveys, a tool allowing the patient to store a plurality of photos and create a photo journal of progress of the patient as he or she loses weight, and a tool allowing the patient to create virtual images based on height, weight and body type.

9. The computer-based weight loss system according to claim 7, wherein the nutrition focused section includes a food diary tool and a recipes tool.

10. The computer-based weight loss system according to claim 9, wherein the food diary tool allows patients to track what and where they eat, their mood during meals, how well food was tolerated and if the food was planned.

11. The computer-based weight loss system according to claim 9, wherein the recipes tool includes access to gastric band-friendly recipes.

12. The computer-based weight loss system according to claim 7, wherein the fitness focused section includes a fitness planning tool and a fitness diary tool.

13. The computer-based weight loss system according to claim 7, wherein the personal plan focused section includes a tool allowing patients to elect to be notified of appointments and reminded of tasks critical to success by electronic means, a tool encouraging patients to focus on preplanned meals, a tool allowing patients to identify times they are most apt to eat for reasons other than hunger, a tool allowing patients to develop coping strategies for potential stumbling blocks, and a tool allowing patients to identify family, friends and healthcare providers they rely upon the most.

14. The computer-based weight loss system according to claim 2, wherein the medical practitioner interface includes a medical practice homepage where the medical practitioner is provided with practice statistics and navigation tools including information on patient registration, alerts, frequency of use, and how many pounds patients have lost using a designated gastric band procedure.

15. The computer-based weight loss system according to claim 2, wherein the medical practitioner interface includes a patient's food diary tool, an alert tool, a gastric band adjustment tool and a patient activity level tool.

16. The computer-based weight loss system according to claim 2, wherein the medical practitioner interface provides an alert tool.

17. The computer-based weight loss system according to claim 16, wherein the alert tool allows medical practitioners to identify issues they may want to address with their patients.

18. The computer-based weight loss system according to claim 17, wherein the alert tool includes alerts relating to a band adjustment survey, a predetermined increment of weight loss, a weight gain over a predetermined time period, a weight plateau for a predetermined time period, no band adjustment for a predetermined time period after surgery, a changed practice affiliation, no logged weight for a predetermined time period, or no logged site access for a predetermined time period.

* * * * *